United States Patent
Zhong et al.

(10) Patent No.: US 9,867,373 B2
(45) Date of Patent: Jan. 16, 2018

(54) FUNGICIDAL COMPOSITION HAVING SYNERGISTIC EFFECT

(71) Applicant: JIANGSU HUIFENG AGROCHEMICAL CO., LTD., Dafeng, Jiangsu (CN)

(72) Inventors: Hangen Zhong, Dafeng (CN); Hongjin Ji, Dafeng (CN)

(73) Assignee: JIANGSU HUIFENG AGROCHEMICAL CO., LTD., Dafeng (CN)

( * ) Notice: Subject to any disclaimer, the term of this patent is extended or adjusted under 35 U.S.C. 154(b) by 0 days.

(21) Appl. No.: 14/889,924

(22) PCT Filed: Jun. 13, 2013

(86) PCT No.: PCT/CN2013/077180
§ 371 (c)(1),
(2) Date: Nov. 9, 2015

(87) PCT Pub. No.: WO2014/180020
PCT Pub. Date: Nov. 13, 2014

(65) Prior Publication Data
US 2016/0113280 A1    Apr. 28, 2016

(30) Foreign Application Priority Data

May 7, 2013 (CN) .......................... 2013 1 0165069

(51) Int. Cl.
| A01N 47/44 | (2006.01) |
| A01N 43/653 | (2006.01) |
| A01N 43/84 | (2006.01) |
| A01N 37/18 | (2006.01) |
| A01N 43/54 | (2006.01) |
| A01N 43/50 | (2006.01) |
| A01N 47/38 | (2006.01) |
| A01N 47/10 | (2006.01) |

(52) U.S. Cl.
CPC .............. *A01N 47/44* (2013.01); *A01N 37/18* (2013.01); *A01N 43/50* (2013.01); *A01N 43/54* (2013.01); *A01N 43/653* (2013.01); *A01N 43/84* (2013.01); *A01N 47/10* (2013.01); *A01N 47/38* (2013.01)

(58) Field of Classification Search
CPC ........ A01N 47/44; A01N 43/54; A01N 47/38; A01N 37/18; A01N 43/50; A01N 43/653; A01N 43/84; A01N 47/10
See application file for complete search history.

(56) References Cited

U.S. PATENT DOCUMENTS

| 5,420,148 A | 5/1995 | Dehne et al. |
| 5,504,100 A | 4/1996 | Dehne et al. |
| 5,585,393 A | 12/1996 | Dehne et al. |
| 5,668,163 A | 9/1997 | Dehne et al. |
| 6,624,183 B2 | 9/2003 | Wachendorff-Neumann et al. |
| 7,115,593 B2 | 10/2006 | Wachendorff-Neumann et al. |
| 7,208,510 B2 | 4/2007 | Wachendorff-Neumann et al. |
| 7,956,009 B2 | 6/2011 | Wachendorff-Neumann et al. |
| 2003/0105146 A1 | 6/2003 | Wachendorff-Neumann et al. |
| 2004/0029840 A1 | 2/2004 | Wachendorff-Neumann et al. |
| 2004/0234492 A1 | 11/2004 | Stockel |
| 2006/0172981 A1 | 8/2006 | Wachendorff-Neumann et al. |
| 2006/0217447 A1* | 9/2006 | Blow ................. A01N 31/12 514/735 |
| 2006/0276468 A1* | 12/2006 | Blow ................. A01N 43/50 514/232.5 |
| 2007/0161688 A1 | 7/2007 | Wachendorff-Neumann et al. |
| 2012/0244095 A1* | 9/2012 | Konradi ............. A61Q 17/00 424/61 |

FOREIGN PATENT DOCUMENTS

| CN | 1335062 A | 2/2002 |
| CN | 1409596 A | 4/2003 |
| CN | 1671868 A | 9/2005 |

(Continued)

OTHER PUBLICATIONS

Cyprodinil data sheet from www.alanwood.net, accessed Sep. 14, 2017.*
prochloraz data sheet from www.alanwood.net, accessed Sep. 14, 2017.*
Jan. 30, 2014 International Search Report issued in International Patent Application No. PCT/CN2013/077180.
Jan. 30, 2014 Written Opinion issued in International Patent Application No. PCT/CN2013/077180.
Nov. 10, 2015 International Preliminary Report on Patentability issued in International Patent Application No. PCT/CN2013/077180.

*Primary Examiner* — Sarah Pihonak
*Assistant Examiner* — Jason Deck
(74) *Attorney, Agent, or Firm* — Oliff PLC

(57) ABSTRACT

A fungicidal composition having a synergistic effect is provided. The composition includes active ingredients A and B. The active ingredient A is polyhexamethylene biguanide or an agriculturally acceptable salt thereof, the active ingredient B is one selected from cyprodinil, epoxiconazole, benthiavalicarb-isopropyl, zoxamide, azoxystrobin, prothioconazole, difenoconazole, fenamidone, polyoxin, iprodione, acibenzolar, dithianon, pyraclostrobin, trifloxystrobin, picoxystrobin, fluazinam, thifluzamide or dimethomorph, and the weight ratio of the two ingredients is from 1:50 to 50:1. The test results show that the fungicidal composition according to the present invention has an obvious synergistic effect, and importantly, the application rate is reduced, such that the cost is lowered. The application rate of a single agent alone is effectively reduced by combining the fungicides of different mechanisms and modes of action, which is beneficial for broadening the fungicidal spectrum, retarding the resistance development of the fungi and improving the control effect.

8 Claims, No Drawings

FOREIGN PATENT DOCUMENTS

| | | |
|---|---|---|
| CN | 101962442 A | 2/2011 |
| CN | 102461653 A | 5/2012 |
| EP | 0630570 A2 | 12/1994 |
| EP | 2433987 A1 | 3/2012 |
| WO | 2004/011682 A1 | 2/2004 |
| WO | WO 2007027859 A1 * | 3/2007 ........... C08K 5/0058 |
| WO | WO 2010097639 A2 * | 9/2010 ............ A01N 33/12 |
| WO | 2011/030094 A2 | 3/2011 |

* cited by examiner

FUNGICIDAL COMPOSITION HAVING SYNERGISTIC EFFECT

BACKGROUND

Technical Field

The present invention belongs to the field of agricultural plant protection, and particularly relates to a fungicidal composition with improved performances, and more particularly to a fungicidal composition comprising.

Related Art

Polyhexamethylene biguanide is a broad-spectrum antifungal agent developed by Aveciago Corporation (UK) that is generally recognized as the most safe and effective anti-fungal agent in 21th centenary. It is colorless and odorless, has a low application rate, a broad spectrum, a low toxicity, fast onset of action, and a low foaming performance, can form a layer of cations on the surface of an article after application to exert a fungal inhibition effect for a long period of time without causing resistance development in fungi, and is considered to be safe by FDA and EPA. The median lethal dose LD50 of polyhexamethylene biguanide to mice is above 5000 mg/kg, thus being actually non-toxic. When used as a cationic fungicide in the agricultural area, polyhexamethylene biguanide can rapidly adsorbed onto the surface of fungal cells, and attack and destroy the cytoplasmic membrane quickly, such that the cytoplasm is leaked, thereby achieving an optimum fungicidal and sterile effect, to remove the pathogens and viruses completely. The common derivatives include, for example, polyhexamethylene biguanide hydrochloride.

Cyprodinil is a broad-spectrum fungicide that has an obvious control effect on the diseases on a variety of crops caused by the fungi of Ascomycetes and Deuteromycetes, and may be used in admixture with most of the bactericides, fungicides, insecticides, and herbicides, to achieve a good control effect. Cyprodinil has curative and eradicant effects on various diseases of field crops, fruits and vegetables, turf and ornamentals.

Epoxiconazole is a systemic triazole fungicide, the mechanism of action of which is inhibiting the synthesis of ergosterol in, and hindering the formation of cell wall of the harmful fungi. Epoxiconazole has not only good protective, curative and eradicant activities, but also systemic and good residual activities. Epoxiconazole can improve the chitinase activity of the crops, cause the shrinkage of the fungal haustoria, and inhibit the invasion of harmful fungi, which is unique to epoxiconazole among all the triazole products. Epoxiconazole has a good control effect on the leaf spot, powdery mildew, and rust disease on bananas, alliums, celeries, common beans, melons, asparagus, peanuts, and sugar beets, and anthracnose and white rot of grape, etc.

Benthiavalicarb-isopropyl has a strong preventive, curative, and penetration activity, and has a good persistence and rainfastness. In field trials, benthiavalicarb-isopropyl can effectively control the late blight of potatoes and tomatoes and the downy mildew of grape and other crops at a low application rate. When mixed with other fungicides, benthiavalicarb-isopropyl also has a quite good efficacy for harmful fungi.

Zoxamide is a new broad-spectrum fungicide, which is mainly used for controlling and treating various bacterial and fungal diseases including downy mildew on cucumbers, black spot on pears, scab on apples, anthracnose on citrus, anthracnose on grapes, and others. The mechanisms of fungicidal action mainly include destroying the nuclei structure of the harmful fungi to cause they to die due to lose of the core component, and interfering with the metabolism of the fungal cells to cause physiological disturbance, thus ultimately leading to death.

Azoxystrobin is a highly potent and broad-spectrum methoxyacrylate fungicide, which has a good activity for the diseases caused by almost all the fungi (including Ascomycotina, Basidiomycotina, Mastigomycotina, and Deuteromycotina), such as powdery mildew, rust, glume blight, net blotch, downy mildew, and rice blast. Azoxystrobin is useful in stem and leaf spray, seed treatment, and also soil treatment, and mainly used for cereals, rice, peanuts, grape, potatoes, fruit trees, vegetables, coffee, and turf etc.

Prothioconazole is a new broad-spectrum triazolthione fungicide developed by Bayer Company, which is mainly used for controlling numerous diseases of cereals, wheat and barley, beans and other crops. Prothioconazole has a low toxicity, no teratogenicity and mutagenicity, and is non-toxic to embryos and safe for human and environment. The mechanism of action is inhibiting the demethylation at position 14 of lanosterol or 2,4-methylene dihydrolanosterol that is a precursor of sterol in fungi.

Difenoconazole is a systemic triazole fungicide, which is a sterol demethylation inhibitor that can systemically absorbed inside the leaves of the plants, has a very high re-distribution ability, and can preclude the invasion of harmful fungi and prevent the spread of the disease spot, thus having a good protective and curative effect. Difenoconazole is particularly effective for powdery mildew, rust, leaf spot, black spot scab, and anthracnose of a variety of crops.

Fenamidone has similar mechanism of action and features to those of famoxadone and methoxyacrylate fungicides, that is, through inhibition of mitochondrial respiration by retarding the electron transfer at coenzyme Q for hydrogenation-cytochrome C oxidoreductase level. Fenamidone is applicable to wheat, cotton, grape, tobacco, turf, sunflower, rose, potato, tomato, and other vegetables for controlling various diseases including downy mildew, blight, *phytophthora* blight, damping-off, black spot, and mottled rot.

Polyoxin is a metabolic product from *S. aureofaciens*, which is a broad-spectrum antibiotic fungicide having a good systemic translocation effect. The mechanism of action is interfering with the biosynthesis of chitin in cell wall of the harmful fungi, thus leading to the death of harmful fungi due to the failure to biosynthesis of the thallus cell wall. After contacting the agent, the germ tube and filament are locally expanded and ruptured, such that the cells cannot develop normally due to the leakage of cell content, which ultimately leads to the cell death. Therefore, polyoxin also functions to inhibit the spore formation of the harmful fungi and the spread of the disease spots.

Iprodione is a dicarboximide high-potent, broad-spectrum, contact fungicide that has a curative and protective effect and also a systemic action through root uptake. Iprodione can effectively control fungi that are resistant to systemic benzimidazole fungicides, and is suitable for controlling early defoliation, grey mold, early blight and so on of a variety of fruit trees, vegetables, melons and other crops.

Acibenzolar is a high potent, broad-spectrum, new fungicide, which has a good control effect on powdery mildew of strawberries, melons, and cucumbers, black spot of pears, and other diseases. Acibenzolar has both a broad-spectrum fungicidal activity and a good protective and curative effect and no cross resistance to other commonly used fungicides, and is longer lasting than conventional fungicides. Acibenzolar is highly selective, safe for crops, human, livestock, and beneficial organisms, and substantially causes no pollution to environment.

Dithianon is a protective fungicide for many diseases on leaves of a variety of pome fruits and stone fruits and has multiple mechanisms of action. Dithianon inhibits a series of fungal enzymes by reacting with a sulfur containing group and interferes with cell respiration, ultimately leading to the death of harmful fungi. Dithianon has both a good protective activity and a certain curative activity. The suitable fruit trees include pome fruits and stone fruits, for example, apples, pears, peaches, apricots, cherries, citrus, coffee, grapes, strawberries, and hops. Dithianon is effective in controlling almost all the diseases of fruit trees such as black spot, mildew bite, leaf spot, rust, anthracnose, scab, downy mildew, and brown rot, except for powdery mildew.

Pyraclostrobin is a new broad-spectrum fungicide. The mechanism of action includes inhibition of the mitochondrial respiration by hindering the electron transfer during cytochrome synthesis. Pyraclostrobin has protective, curative, and leaf-penetrating translocation effects. The field efficacy test results show that the pyraclostrobin concentrate has a good control effect on powdery mildew and downy mildew of cucumber and black spot and leaf spot of bananas.

Trifloxystrobin is a new fluorine-containing fungicide successfully developed with the natural product strobilurin as a lead fungicide compound. Trifloxystrobin is characterized by high efficacy, broad spectrum, protective, curative, eradicant, penetrating and systemic activities, and long persistence, is effective for strains resistant to 1,4-demethylase inhibitors, benzamides, dicarboximides and benzimidazoles, and has no cross resistance to existing fungicides.

Picoxystrobin is a systemic broad-spectrum fungicide, which is mainly used for controlling leaf diseases of wheat and barley, for example, leaf blight, leaf rust, glume blight, brown spot, and powdery mildew. Compared with other methoxyacrylate fungicides, picoxystrobin has a more potent curative effect for leaf blight, net blotch, and leaf blotch of wheat.

Fluazinam is a 2,6-dinitroaniline protective fungicide, which can control the disease caused by *Botrytis cinerea* when applied at a dosage of 50-100 g(a.i.)/100 L. Fluazinam is quite effective for *Alternaria* spp, *Botrytis* spp, *Phytophthora* spp, *Plasmopara* spp, *Sclerotinia* spp, and *Nigrospora* spp, is highly effective for *Botrytis cinerea* resistant to benzimidazole and dicarboximide fungicides, and has long persistence and good rainfastness. Moreover, fluazinam also has a good control effect for phytophagous mites, crucifer club root, and rice damping-off caused by *Rhizopus* spp.

Thifluzamide is a thiazole-carboxamide fungicide, which has a strong systemic translocation performance and a long persistence. Thifluzamide is a succinate dehydrogenase inhibitor, which is highly competitive during a biochemical process due to the inclusion of fluorine. The process cannot be reversed once thifluzamide is bound to a substrate or an enzyme. Thifluzamide is active for the harmful fungi from *Rhizoctonia, Puccinia, Ustilago, Tilletia, Peniophora*, and *Pyrenophora*, and is particularly effective for the diseases caused by the fungi of Basidiomycetes, such as sheath blight and seedling blight.

Dimethomorph is a morpholine broad-spectrum fungicide, which has a unique mode of action for fungi of the genus *Phytophthora* of the family Peronosporaceae of the class Phycomycetes, mainly by causing the breakdown of the sporangia wall, thus leading to the death of the fungi. Dimethomorph is a specialized fungicide for the fungi of the class Oomycetes, and features destruction of the formation of cell wall and membrane. Dimethomorph has impact on each stage of the life cycle of oomycetes, is especially sensitive in the development stage of sporangiophore and oospore, can exert an inhibitory effect at an extremely low concentration (<0.25 µg/ml) and has no cross resistance to phenylamide agents.

It is showed in practical use of pesticides that the repeated and exclusive application of one active compound to control the harmful fungi will result in the occurrence of rapid selectivity of the fungus strain in most cases. At present, the harmful fungi are controlled by using mixtures of compounds with different activities for the purpose of reducing the hazard of the selectivity of the resistant fungus strain. By combining active compounds having different mechanisms of action, the resistance development can be slowed down, the application rate is reduced, and thus the control cost is lowered.

SUMMARY

In view of the technical problems above of resistance and persistence in soil of the fungicides in practical use, two fungicides of different mechanisms of fungicidal action are screened out and combined, to improve the control effect of the fungicides, retard the resistance development, reduce the application rate, and lower the control cost.

To solve the above technical problems, the present invention provides a fungicidal composition having a synergistic effect. The composition comprises active ingredients A and B. The active ingredient A is polyhexamethylene biguanide or an agriculturally acceptable salt thereof, the active ingredient B is one selected from cyprodinil, epoxiconazole, benthiavalicarb-isopropyl, zoxamide, azoxystrobin, prothioconazole, difenoconazole, fenamidone, polyoxin, iprodione, acibenzolar, dithianon, pyraclostrobin, trifloxystrobin, picoxystrobin, fluazinam, thifluzamide, and dimethomorph. The inventors find through tests that the fungicidal composition has an obvious synergistic effect, and importantly, the application rate is reduced, such that the cost is lowered. The ingredients A and B have different chemical structures and distinct mechanisms of action, by which the fungicidal spectrum can be greatly broadened and the occurrence and development rate of resistance of the pathogens can be delayed to some extent when combined. Moreover, the ingredients A and B have no cross resistance.

The composition of the present invention may consist essentially of, or consist of the ingredients A and B. In the fungicidal composition, the weight ratio of the ingredients A and B is 1:50-50:1, preferably 1:30-30:1, and more preferably 1:10-10:1.

As required by the production and application techniques, in the present invention, polyhexamethylene biguanide may exist as a salt thereof. It is found through comparison in tests that there is no obvious difference between the control effects of polyhexamethylene biguanide and salts thereof. The useful salt of polyhexamethylene biguanide in the present invention is one of polyhexamethylene biguanide hydrochloride, polyhexamethylene biguanide nitrate, polyhexamethylene biguanide carbonate, polyhexamethylene biguanide phosphate, polyhexamethylene biguanide sulfate, polyhexamethylene biguanide stearate, and polyhexamethylene biguanide acetate. Preferred is polyhexamethylene biguanide hydrochloride represented by a formula below:

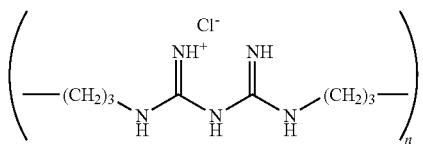

where n=12 or 16.

The fungicidal composition according to the present invention may further be comprised of the active ingredients and pesticide adjuvants, where the amount of the active ingredient may be selected as required by specific conditions. For example, the fungicidal composition according to the present invention comprises 6-92% by weight of the active ingredients and 94-8% by weight of the pesticide adjuvants. The fungicidal composition is prepared into pesticidally acceptable formations, for example a powder or a wettable powder, with the active ingredients and the pesticide adjuvants.

The present invention provides use of the fungicidal composition comprising the ingredients A (polyhexamethylene biguanide or an agriculturally acceptable salt thereof) and B in the control of diseases on crops in the agricultural area, and especially in the control of cucumber downy mildew or wheat rust.

When used in controlling the diseases on crops, the fungicidal composition of the present invention may be optionally used for seed impregnation, sprayed onto the leaves by reconstitution with water during the growth period of the crops, or applied onto the surface of the target objects, depending on the different diseases to be controlled.

The composition may further comprise a carrier, an adjuvant and/or a surfactant. A commonly used adjuvant may be blended during application.

The suitable adjuvant may be a solid or liquid that is generally a material commonly used in the preparation of formulations, for example, a natural or regenerated mineral substance, a solvent, a dispersing agent, a wetting agent, an adhesive, a thickener, a binder or a fertilizer.

The composition of the present invention may be applied by administering the composition of the present invention to the aboveground parts of plants, in particular to the leaves or leaf surface thereof. The application frequency and rate depend on the pathogen biology and the climatic and maintenance conditions. The locus where the plant is growing, for example paddy field, may be impregnated with a liquid formulation of the composition, or the composition is incorporated in solid form into the soil, for example, in granular form (soil application) or penetrates the plant through the roots via the soil (systemic action). Alternatively, the occurrence of diseases may be eradicated and prevented by coating or immersing the seeds.

The composition may be used by applying the active ingredients alone or in admixture with additives. Therefore, the composition of the present invention may be prepared into various formulations, for example, a wettable powder, a suspension, an oily suspension, water dispersible granules, an aqueous emulsion, or a microemulsion. Depending on the properties of the compositions, the objectives intended to be achieved by applying the compositions, and the environmental conditions, the compositions may be applied by spraying, atomizing, dusting, scattering, or pouring.

The composition of the present invention may be prepared into various formulations through known processes. The active ingredients may be uniformly mixed with an adjuvant such as a solvent or a solid carrier and a surfactant if needed, and ground to prepare a desired formulation.

The solvent may be selected from aromatic hydrocarbons containing preferably 8 to 12 carbon atoms, for example, a xylene mixture, substituted benzene, or a phthalate ester, for example, dibutyl or dioctyl phthalate; aliphatic hydrocarbons, for example, cyclohexane or paraffin; alcohols, glycols and ethers and esters thereof, for example, ethanol, ethylene glycol, and ethylene glycol monomethyl ether; ketones, for example, cyclohexanone; high-polarity solvents, for example, N-methyl-2-pyrrolidone, dimethyl sulfoxide, or dimethyl formamide; and vegetable oils, for example, soy bean oil.

The solid carrier includes for example natural mineral fillers generally used for powders and dispersible powders, for example, talc, kaolin, montmorillonite or activated bauxite. To manage the physical properties of the composition, highly dispersive silicic acid or highly dispersive absorbent polymer carrier may also be added, for example, granular adsorptive carrier or non-adsorptive carrier. The suitable granular adsorptive carrier is porous, for example, pumice, soapy clay or bentonite. The suitable non-adsorptive carrier includes for example calcite or sand. Moreover, a large amount of inorganic or organic material that is pre-prepared into granules and especially dolomite may be used as the carrier.

As desired by the chemical nature of the active ingredients in the composition according to the present invention, the suitable surfactant includes lignin sulfonic acid, naphthalenesulfonic acid, phenolsulfonic acid, alkaline earth metal or amine salts, alkylarylsulfonates, alkylsulfates, alkylsulfonates, fatty alcohol sulfates, fatty acids and ethylene glycol sulfated fatty alcohol ethers, condensation products of sulfonated naphthalene and naphthalene derivatives with formaldehyde, condensation products of naphthalene or naphthalenesulfonic acid with phenol and formaldehyde, polyoxyethylene octyl phenyl ethers, ethoxylated iso-octylphenol, octylphenol, nonylphenol, alkylaryl polyethylene glycol ethers, tributylphenyl polyethylene glycol ether, tristearylphenyl polyethylene glycol ether, alkylaryl polyether alcohols, ethoxylated castor oil, polyoxyethylene alkyl ethers, condensation products of ethylene oxide, ethoxylated polyoxypropylene, polyethylene glycol ether laurate acetal, sorbates, waste lignin sulfite liquor, and methyl cellulose.

The two active ingredients in the fungicidal composition of the present invention have a synergistic effect, such that the activity of the composition is obviously higher than the respective activity or expected sum of the respective activity of single compounds alone. The synergistic effect leads to a reduced application rate, a broadened fungicidal spectrum, fast onset of action, and a prolonged control effect, whereby the fungi harmful to plants can be well controlled only by means of one or several applications, and the underlying application interval is widened. These features are particularly important in practice of controlling the fungi harmful to plants.

The fungicidal composition of the present invention exhibits the following additional features. 1. The composition of the present invention has an obvious synergistic effect. 2. Because the two individual agents in the composition of the present invention have highly different structures and completely different mechanisms of action, no cross resistance exists, such that the problem of resistance development occurred due to the use of single agents alone can be retarded. 3. The composition of the present invention is safe for crops, and good in the control effect. It is demonstrated through tests that the fungicidal composition of the present invention has stable chemical properties and a significant synergistic effect since the two active ingredients therein exhibit an obvious synergistic and complementary effect on the target organisms.

DETAILED DESCRIPTION

To make the objectives, technical solutions, and advantages of the present invention clearer, the present invention is described in further detail with reference to examples. It should be understood that specific examples described herein are merely provided for explaining, instead of limiting, the present invention. Any modifications, equivalent replacements, and improvements made without departing from the spirit and principle of the present invention fall within the protection scope of the present invention.

The percentages given in all the formulations in the examples below are all weight percentages. The various formulations are processed from the composition of the present invention by a process known in the prior art which may be varied as desired.

I. Preparation Example Of Formulations (I) Processing of Wettable Powder and Examples The active ingredients polyhexamethylene biguanide or a salt thereof and one of cyprodinil, epoxiconazole, benthiavalicarb-isopropyl, zoxamide, azoxystrobin, prothioconazole, difenoconazole, fenamidone, polyoxin, iprodione, acibenzolar, dithianon, pyraclostrobin, trifloxystrobin, picoxystrobin, fluazinam, thifluzamide, and dimethomorph were fully mixed with various adjuvants and fillers in proportion, and ground by an ultra-fine grinder, to obtain a wettable powder.

Example 1

62% Polyhexamethylene Biguanide Hydrochloride.Cyprodinil Wettable Powder polyhexamethylene biguanide hydrochloride 60%, cyprodinil 2%, a sodium alkyl naphthalene sulfonate 4%, sodium dodecyl sulfonate 3%, ammonium sulfate 3%, and light calcium carbonate q.s. to 100%.

Example 2

50% Polyhexamethylene Biguanide Hydrochloride.Cyprodinil Wettable Powder polyhexamethylene biguanide hydrochloride 25%, cyprodinil 25%, sodium lignin sulfonate 6%, sodium dodecyl sulfonate 3%, xanthan gum 1%, sodium carboxymethyl starch 1%, and attapulgite clay q.s. to 100%.

Example 3

65% Polyhexamethylene Biguanide Hydrochloride.Cyprodinil Wettable Powder polyhexamethylene biguanide hydrochloride 2%, cyprodinil 63%, sodium lignin sulfonate 5%, a sodium methylnaphthalene sulfonate formaldehyde condensate 7%, sodium dodecyl sulfate 3%, and diatomaceous earth q.s. to 100%.

Example 4

85% Polyhexamethylene Biguanide Hydrochloride.Epoxiconazole Wettable Powder polyhexamethylene biguanide hydrochloride 83%, epoxiconazole 2%, ammonium sulfate 1%, sodium alginate 2%, a sodium methylnaphthalene sulfonate formaldehyde condensate 1%, organic silicone 1%, and bentonite q.s. to 100%.

Example 5

30% Polyhexamethylene Biguanide Acetate.Epoxiconazole Wettable Powder polyhexamethylene biguanide acetate 15%, epoxiconazole 15%, sodium dodecyl sulfonate 2%, a sodium alkyl naphthalene sulfonate 2%, ammonium sulfate 3%, and light calcium carbonate q.s. to 100%.

Example 6

75% Polyhexamethylene Biguanide Carbonate.Epoxiconazole Wettable Powder polyhexamethylene biguanide carbonate 2%, epoxiconazole 73%, a sodium methylnaphthalene sulfonate formaldehyde condensate 5%, sodium lignin sulfonate 4%, sodium dodecyl sulfate 3%, and diatomaceous earth q.s. to 100%.

Example 7

62% Polyhexamethylene Biguanide Hydrochloride Benthiavalicarb-Isopropyl Wettable Powder polyhexamethylene biguanide hydrochloride 60%, benthiavalicarb-isopropyl 2%, sodium carboxymethyl starch 1%, sodium dodecyl sulfonate 4%, sodium lignin sulfonate 4%, xanthan gum 1%, and attapulgite clay q.s. to 100%.

Example 8

40% Polyhexamethylene Biguanide Stearate.Benthiavalicarb-Isopropyl Wettable Powder polyhexamethylene biguanide stearate 20%, benthiavalicarb-isopropyl 20%, ammonium sulfate 1%, sodium alginate 2%, a sodium methylnaphthalene sulfonate formaldehyde condensate 1%, organic silicone 1%, and bentonite q.s. to 100%.

Example 9

75% Polyhexamethylene Biguanide.Benthiavalicarb-Isopropyl Wettable Powder polyhexamethylene biguanide 2%, benthiavalicarb-isopropyl 73%, a sodium methylnaphthalene sulfonate formaldehyde condensate 5%, sodium lignin sulfonate 4%, sodium dodecyl sulfate 3%, and diatomaceous earth q.s. to 100%.

Example 10

85% Polyhexamethylene Biguanide Hydrochloride.Zoxamide Wettable Powder polyhexamethylene biguanide hydrochloride 82%, zoxamide 3%, calcium lignin sulfonate 2%, sodium dodecylbenzene sulfonate 1%, bentonite 2%, and attapulgite clay q.s. to 100%.

Example 11

60% Polyhexamethylene Biguanide.Zoxamide Wettable Powder polyhexamethylene biguanide 30%, zoxamide 30%, an alkylpolyoxyethylene ether sulfonate 1%, nekal 2%, bentonite 1.5%, white carbon black 2%, and diatomaceous earth q.s. to 100%.

Example 12

75% Polyhexamethylene Biguanide Sulfate.Zoxamide Wettable Powder polyhexamethylene biguanide sulfate 2%, zoxamide 73%, an alkylsulfonate 6%, sodium lignin sulfonate 6%, white carbon black 5%, and kaolin q.s. to 100%.

Example 13

88% Polyhexamethylene Biguanide Hydrochloride.Azoxystrobin Wettable Powder polyhexamethylene biguanide hydrochloride 86%, azoxystrobin 2%, a polyoxyethylene octyl phenyl ether 2%, sodium lignin sulfonate 6%, white carbon black 4%, and diatomaceous earth q.s. to 100%.

Example 14

50% Polyhexamethylene Biguanide.Azoxystrobin Wettable Powder polyhexamethylene biguanide 25%, azoxystrobin 25%, calcium lignin sulfonate 7%, white carbon black 5%, sodium dodecylbenzene sulfonate 3%, and attapulgite clay q.s. to 100%.

Example 15

62% Polyhexamethylene Biguanide Acetate.Azoxystrobin Wettable Powder polyhexamethylene biguanide acetate 2%, azoxystrobin 60%, calcium lignin sulfonate 5%, bentonite 4%, a polyoxyethylene octyl phenyl ether 3%, and attapulgite clay q.s. to 100%.

Example 16

85% Polyhexamethylene Biguanide Hydrochloride.Prothioconazole Wettable Powder polyhexamethylene biguanide hydrochloride 83%, prothioconazole 2%, a polyoxyethylene octyl phenyl ether 1%, sodium lignin sulfonate 2%, white carbon black 3%, and diatomaceous earth q.s. to 100%.

Example 17

50% Polyhexamethylene Biguanide.Prothioconazole Wettable Powder polyhexamethylene biguanide 25%, prothioconazole 25%, sodium dodecylbenzene sulfonate 3%, white carbon black 5%, calcium lignin sulfonate 7%, and attapulgite clay q.s. to 100%.

Example 18

85% Polyhexamethylene Biguanide Stearate.Prothioconazole Wettable Powder polyhexamethylene biguanide stearate 3%, prothioconazole 82%, calcium lignin sulfonate 5%, bentonite 4%, a polyoxyethylene octyl phenyl ether 3%, and attapulgite clay q.s. to 100%.

Example 19

88% Polyhexamethylene Biguanide.Difenoconazole Wettable Powder polyhexamethylene biguanide 86%, difenoconazole 2%, sodium dodecylbenzene sulfonate 2%, bentonite 1%, calcium lignin sulfonate 2%, and attapulgite clay q.s. to 100%.

Example 20

50% Polyhexamethylene Biguanide Carbonate.Difenoconazole Wettable Powder polyhexamethylene biguanide carbonate 25%, difenoconazole 25%, sodium lignin sulfonate 6%, an alkylsulfonate 6%, white carbon black 11%, and kaolin q.s. to 100%.

Example 21

86% Polyhexamethylene Biguanide Hydrochloride.Difenoconazole Wettable Powder polyhexamethylene biguanide hydrochloride 2%, difenoconazole 84%, nekal 1%, an alkylpolyoxyethylene ether sulfonate 2%, bentonite 1.5%, white carbon black 2%, and diatomaceous earth q.s. to 100%.

Example 22

62% Polyhexamethylene Biguanide Hydrochloride.Fenamidone Wettable Powder polyhexamethylene biguanide hydrochloride 60%, fenamidone 2%, a sodium alkyl naphthalene sulfonate 4%, sodium dodecyl sulfonate 3%, ammonium sulfate 3%, and light calcium carbonate q.s. to 100%.

Example 23

50% Polyhexamethylene Biguanide Acetate.Fenamidone Wettable Powder polyhexamethylene biguanide hydrochloride 25%, fenamidone 25%, sodium lignin sulfonate 6%, sodium dodecyl sulfonate 3%, xanthan gum 1%, sodium carboxymethyl starch 1%, and attapulgite clay q.s. to 100%.

Example 24

65% Polyhexamethylene Biguanide Hydrochloride.Fenamidone Wettable Powder polyhexamethylene biguanide hydrochloride 2%, fenamidone 63%, sodium lignin sulfonate 5%, a sodium methylnaphthalene sulfonate formaldehyde condensate 7%, sodium dodecyl sulfate 3%, and diatomaceous earth q.s. to 100%.

Example 25

85% Polyhexamethylene Biguanide Hydrochloride.Polyoxin Wettable Powder polyhexamethylene biguanide hydrochloride 83%, polyoxin 2%, sodium alginate 3%, ammonium sulfate 2%, a sodium methylnaphthalene sulfonate formaldehyde condensate 1%, organic silicone 1%, and bentonite q.s. to 100%.

Example 26

30% Polyhexamethylene Biguanide Acetate.Polyoxin Wettable Powder polyhexamethylene biguanide acetate 15%, polyoxin 15%, sodium dodecyl sulfonate 2%, a sodium alkyl naphthalene sulfonate 2%, ammonium sulfate 3%, and light calcium carbonate q.s. to 100%.

Example 27

75% Polyhexamethylene Biguanide Carbonate.Polyoxin Wettable Powder polyhexamethylene biguanide carbonate 2%, polyoxin 73%, a sodium methylnaphthalene sulfonate formaldehyde condensate 5%, sodium lignin sulfonate 4%, sodium dodecyl sulfate 3%, and diatomaceous earth q.s. to 100%.

Example 28

62% Polyhexamethylene Biguanide Hydrochloride.Iprodione Wettable powder polyhexamethylene biguanide hydrochloride 60%, iprodione 2%, ammonium sulfate 3%, sodium carboxymethyl starch 1%, sodium dodecyl sulfonate 4%, sodium lignin sulfonate 4%, xanthan gum 1%, and attapulgite clay q.s. to 100%.

Example 29

40% Polyhexamethylene Biguanide Stearate.Iprodione Wettable Powder polyhexamethylene biguanide stearate 20%, iprodione 20%, ammonium sulfate 1%, sodium alginate 2%, a sodium methylnaphthalene sulfonate formaldehyde condensate 1%, organic silicone 1%, and bentonite q.s. to 100%.

Example 30

75% Polyhexamethylene Biguanide.Iprodione Wettable Powder polyhexamethylene biguanide 2%, iprodione 73%, a sodium methylnaphthalene sulfonate formaldehyde condensate 5%, sodium lignin sulfonate 4%, sodium dodecyl sulfate 3%, and diatomaceous earth q.s. to 100%.

Example 31

85% Polyhexamethylene Biguanide Hydrochloride.Acibenzolar Wettable Powder polyhexamethylene biguanide hydrochloride 82%, acibenzolar 3%, calcium lignin sulfonate 2%, sodium dodecylbenzene sulfonate 1%, bentonite 2%, and attapulgite clay q.s. to 100%.

Example 32

60% Polyhexamethylene Biguanide.Acibenzolar Wettable Powder polyhexamethylene biguanide 30%, acibenzolar 30%, an alkylpolyoxyethylene ether sulfonate 1%, nekal 2%, bentonite 1.5%, white carbon black 2%, and diatomaceous earth q.s. to 100%.

Example 33

78% Polyhexamethylene Biguanide Sulfate.Acibenzolar Wettable Powder polyhexamethylene biguanide sulfate 2%, acibenzolar 76%, an alkylsulfonate 2%, sodium lignin sulfonate 2%, white carbon black 3%, and kaolin q.s. to 100%.

Example 34

88% Polyhexamethylene Biguanide Hydrochloride.Dithianon Wettable Powder polyhexamethylene biguanide hydrochloride 86%, dithianon 2%, a polyoxyethylene octyl phenyl ether 2%, sodium lignin sulfonate 6%, white carbon black 4%, and diatomaceous earth q.s. to 100%.

Example 35

50% Polyhexamethylene Biguanide.Dithianon Wettable Powder polyhexamethylene biguanide 25%, dithianon 25%, calcium lignin sulfonate 7%, white carbon black 5%, sodium dodecylbenzene sulfonate 3%, and attapulgite clay q.s. to 100%.

Example 36

65% Polyhexamethylene Biguanide Acetate.Dithianon Wettable Powder polyhexamethylene biguanide acetate 2%, dithianon 63%, bentonite 5%, calcium lignin sulfonate 3%, a polyoxyethylene octyl phenyl ether 3%, and attapulgite clay q.s. to 100%.

Example 37

85% Polyhexamethylene Biguanide Hydrochloride.Pyraclostrobin Wettable Powder polyhexamethylene biguanide hydrochloride 83%, pyraclostrobin 2%, a polyoxyethylene octyl phenyl ether 1%, sodium lignin sulfonate 3%, white carbon black 6%, and diatomaceous earth q.s. to 100%.

Example 38

50% Polyhexamethylene Biguanide.Pyraclostrobin Wettable Powder polyhexamethylene biguanide 25%, pyraclostrobin 25%, sodium dodecylbenzene sulfonate 3%, white carbon black 8%, calcium lignin sulfonate 5%, and attapulgite clay q.s. to 100%.

Example 39

82% Polyhexamethylene Biguanide Stearate.Pyraclostrobin Wettable Powder polyhexamethylene biguanide stearate 2%, pyraclostrobin 80%, calcium lignin sulfonate 5%, bentonite 4%, a polyoxyethylene octyl phenyl ether 3%, and attapulgite clay q.s. to 100%.

Example 40

88% Polyhexamethylene Biguanide.Trifloxystrobin Wettable Powder polyhexamethylene biguanide 86%, trifloxystrobin 2%, sodium dodecylbenzene sulfonate 2%, bentonite 1%, calcium lignin sulfonate 2%, and attapulgite clay q.s. to 100%.

Example 41

50% Polyhexamethylene Biguanide Carbonate.Trifloxystrobin Wettable Powder polyhexamethylene biguanide carbonate 25%, trifloxystrobin 25%, sodium lignin sulfonate 6%, an alkylsulfonate 6%, white carbon black 11%, and kaolin q.s. to 100%.

Example 42

86% Polyhexamethylene Biguanide Hydrochloride.Trifloxystrobin Wettable Powder polyhexamethylene biguanide hydrochloride 2%, trifloxystrobin 84%, nekal 1%, an alkylpolyoxyethylene ether sulfonate 2%, bentonite 1.5%, white carbon black 2%, and diatomaceous earth q.s. to 100%.

Example 43

62% Polyhexamethylene Biguanide Hydrochloride.Picoxystrobin Wettable Powder polyhexamethylene biguanide hydrochloride 60%, picoxystrobin 2%, ammonium sulfate 1%, sodium carboxymethyl starch 3%, sodium dodecyl sulfonate 3%, sodium lignin sulfonate 2%, xanthan gum 1%, and attapulgite clay q.s. to 100%.

Example 44

40% Polyhexamethylene Biguanide Stearate.Picoxystrobin Wettable Powder polyhexamethylene biguanide stearate 20%, picoxystrobin 20%, sodium alginate 4%, ammonium sulfate 2%, a sodium methylnaphthalene sulfonate formaldehyde condensate 1%, organic silicone 1%, and bentonite q.s. to 100%.

Example 45

75% Polyhexamethylene Biguanide.Picoxystrobin Wettable Powder polyhexamethylene biguanide 2%, picoxystrobin 73%, a sodium methylnaphthalene sulfonate formaldehyde condensate 2%, sodium lignin sulfonate 5%, sodium dodecyl sulfate 3%, and diatomaceous earth q.s. to 100%.

Example 46

85% Polyhexamethylene Biguanide Hydrochloride.Fluazinam Wettable Powder polyhexamethylene biguanide hydrochloride 83%, fluazinam 2%, a polyoxyethylene octyl phenyl ether 1%, sodium lignin sulfonate 5%, white carbon black 3%, and diatomaceous earth q.s. to 100%.

Example 47

40% Polyhexamethylene Biguanide.Fluazinam Wettable Powder polyhexamethylene biguanide 20%, fluazinam 20%, calcium lignin sulfonate 5%, white carbon black 9%, sodium dodecylbenzene sulfonate 4%, and attapulgite clay q.s. to 100%.

Example 48

65% Polyhexamethylene Biguanide Acetate.Fluazinam Wettable Powder polyhexamethylene biguanide acetate 2%, fluazinam 63%, bentonite 4%, calcium lignin sulfonate 4%, a polyoxyethylene octyl phenyl ether 3%, and attapulgite clay q.s. to 100%.

Example 49

82% Polyhexamethylene Biguanide Hydrochloride.Thifluzamide Wettable Powder polyhexamethylene biguanide hydrochloride 80%, thifluzamide 2%, a polyoxyethylene octyl phenyl ether 1%, sodium lignin sulfonate 4%, white carbon black 5%, and diatomaceous earth q.s. to 100%.

Example 50

50% Polyhexamethylene Biguanide.Thifluzamide Wettable Powder polyhexamethylene biguanide 25%, thifluzamide 25%, sodium dodecylbenzene sulfonate 2%, white carbon black 5%, calcium lignin sulfonate 6%, and attapulgite clay q.s. to 100%.

Example 51

82% Polyhexamethylene Biguanide Stearate.Thifluzamide Wettable Powder polyhexamethylene biguanide stearate 2%, thifluzamide 80%, calcium lignin sulfonate 4%, bentonite 5%, a polyoxyethylene octyl phenyl ether 2%, and attapulgite clay q.s. to 100%.

Example 52

85% Polyhexamethylene Biguanide.Dimethomorph Wettable Powder polyhexamethylene biguanide 83%, dimethomorph 2%, sodium dodecylbenzene sulfonate 2%, bentonite 1%, calcium lignin sulfonate 2%, and attapulgite clay q.s. to 100%.

Example 53

50% Polyhexamethylene Biguanide Carbonate.Dimethomorph Wettable Powder polyhexamethylene biguanide carbonate 25%, dimethomorph 25%, sodium lignin sulfonate 4%, an alkylsulfonate 5%, white carbon black 10%, and kaolin q.s. to 100%.

Example 54

75% Polyhexamethylene Biguanide Hydrochloride.Dimethomorph Wettable Powder polyhexamethylene biguanide hydrochloride 2%, dimethomorph 73%, nekal 1%, an alkylpolyoxyethylene ether sulfonate 1%, bentonite 2%, white carbon black 3%, and diatomaceous earth q.s. to 100%.

II. Efficacy Test (I) Bioassay Examples

1. Toxicity test of polyhexamethylene biguanide hydrochloride combined respectively with benthiavalicarb-isopropyl, dimethomorph, azoxystrobin, fenamidone, dithianon, polyoxin, zoxamide, acibenzolar, and fluazinam on downy mildew pathogens of cucumber Test target organism: downy mildew pathogens of cucumber Based on the test grade scale, the disease development on the leaves of the whole cucumber plant was investigated, and the disease index and control effect were calculated.

The control effect was converted into probability (y), the concentration of the agents (μg/ml) in solution was converted into a logarithmic value (x), the toxic regression equation and the median inhibition concentration $EC_{50}$ were calculated by east square method, and the toxicity index and the co-toxicity coefficient (CTC) of the agents were calculated by SUN Peiyun method.

Actual toxicity index (ATI)=($EC$50 of standard/$EC$50 of test agent)*100

Theoretical toxicity index (TTI)=toxicity index of agent $A$*percentage content of $A$ in the mixture+toxicity index of agent $B$*percentage content of $B$ in the mixture Co-toxicity coefficient (CTC)=[actual toxicity index (ATI) of the mixture/theoretical toxicity index (TTI) of the mixture]*100

Where CTC≤80, the composition exhibits an antagonistic effect; where 80<CTC<120, the composition exhibits an additive effect, and where CTC≥120, the composition exhibits a synergistic effect.

(1) Toxicity Test of Polyhexamethylene Biguanide Hydrochloride Combined with Benthiavalicarb-Isopropyl on Downy Mildew Pathogens of Cucumber

TABLE 1

Toxicity test result analysis of polyhexamethylene biguanide hydrochloride combined with benthiavalicarb-isopropyl on downy mildew pathogens of cucumber

| Name of agent | $EC_{50}$ (μg/ml) | ATI | TTI | Co-toxicity coefficient (CTC) |
|---|---|---|---|---|
| Polyhexamethylene biguanide hydrochloride | 3.25 | 100.0 | / | / |
| Benthiavalicarb-isopropyl | 5.41 | 60.1 | / | / |
| Polyhexamethylene biguanide hydrochloride:benthiavalicarb-isopropyl = 50:1 | 2.32 | 140.09 | 99.22 | 141.191 |
| Polyhexamethylene biguanide hydrochloride:benthiavalicarb-isopropyl = 30:1 | 1.91 | 170.16 | 98.67 | 172.454 |
| Polyhexamethylene biguanide hydrochloride:benthiavalicarb-isopropyl = 10:1 | 1.58 | 205.69 | 96.37 | 213.438 |
| Polyhexamethylene biguanide hydrochloride:benthiavalicarb-isopropyl = 1:1 | 2.08 | 156.25 | 80.05 | 195.191 |
| Polyhexamethylene biguanide hydrochloride:benthiavalicarb-isopropyl = 1:10 | 2.26 | 143.81 | 63.73 | 225.655 |
| Polyhexamethylene biguanide hydrochloride:benthiavalicarb-isopropyl = 1:30 | 3.79 | 85.75 | 61.43 | 139.589 |

TABLE 1-continued

Toxicity test result analysis of polyhexamethylene biguanide hydrochloride combined with benthiavalicarb-isopropyl on downy mildew pathogens of cucumber

| Name of agent | $EC_{50}$ (µg/ml) | ATI | TTI | Co-toxicity coefficient (CTC) |
|---|---|---|---|---|
| Polyhexamethylene biguanide hydrochloride:benthiavalicarb-isopropyl = 1:50 | 3.93 | 82.70 | 60.88 | 135.841 |

The results (in Table 1) show that the control effect of the combination of polyhexamethylene biguanide hydrochloride with benthiavalicarb-isopropyl on downy mildew of cucumber is significantly improved, suggesting that the combination has an obvious synergistic effect on downy mildew pathogens of cucumber.

(2) Toxicity Test of Polyhexamethylene Biguanide Hydrochloride Combined with Dimethomorph on Downy Mildew Pathogens of Cucumber

TABLE 2

Toxicity test result analysis of polyhexamethylene biguanide hydrochloride combined with dimethomorph on downy mildew pathogens of cucumber

| Name of agent | $EC_{50}$ (µg/ml) | ATI | TTI | Co-toxicity coefficient (CTC) |
|---|---|---|---|---|
| Polyhexamethylene biguanide hydrochloride | 4.08 | 100.0 | / | / |
| Dimethomorph | 6.36 | 63.9 | / | / |
| Polyhexamethylene biguanide hydrochloride:dimethomorph = 50:1 | 2.99 | 136.5 | 99.29 | 137.48 |
| Polyhexamethylene biguanide hydrochloride:dimethomorph = 30:1 | 2.40 | 170.0 | 98.835 | 172.00 |
| Polyhexamethylene biguanide hydrochloride:dimethomorph = 10:1 | 2.12 | 192.4 | 96.718 | 198.93 |
| Polyhexamethylene biguanide hydrochloride:dimethomorph = 1:1 | 2.01 | 203.0 | 81.95 | 247.71 |
| Polyhexamethylene biguanide hydrochloride:dimethomorph = 1:10 | 2.91 | 140.2 | 67.18 | 208.69 |
| Polyhexamethylene biguanide hydrochloride:dimethomorph = 1:30 | 3.33 | 122.5 | 65.17 | 187.97 |
| Polyhexamethylene biguanide hydrochloride:dimethomorph = 1:50 | 4.87 | 83.8 | 64.60 | 129.72 |

The results (in Table 2) show that the control effect of the combination of polyhexamethylene biguanide hydrochloride with dimethomorph on downy mildew of cucumber is significantly improved, suggesting that the combination has an obvious synergistic effect on downy mildew pathogens of cucumber. Especially when polyhexamethylene biguanide or an agriculturally acceptable salt thereof is mixed with dimethomorph at a ratio ranging from 1:30 to 30:1, the co-toxicity coefficient of polyhexamethylene biguanide hydrochloride and dimethomorph is always above 170, and the synergistic effect is obvious.

(3) Toxicity Test of Polyhexamethylene Biguanide Hydrochloride Combined with Azoxystrobin on Downy Mildew Pathogens of Cucumber

TABLE 3

Toxicity test result analysis of polyhexamethylene biguanide hydrochloride combined with azoxystrobin on downy mildew pathogens of cucumber

| Name of agent | $EC_{50}$ (µg/ml) | ATI | TTI | Co-toxicity coefficient (CTC) |
|---|---|---|---|---|
| Polyhexamethylene biguanide hydrochloride | 4.21 | 100.00 | / | / |
| Azoxystrobin | 5.82 | 72.34 | / | / |
| Polyhexamethylene biguanide hydrochloride:azoxystrobin = 50:1 | 3.32 | 126.81 | 99.458 | 127.50 |
| Polyhexamethylene biguanide hydrochloride:azoxystrobin = 30:1 | 3.05 | 138.03 | 99.108 | 139.27 |
| Polyhexamethylene biguanide hydrochloride:azoxystrobin = 10:1 | 2.29 | 183.84 | 97.485 | 188.58 |

TABLE 3-continued

Toxicity test result analysis of polyhexamethylene biguanide hydrochloride combined with azoxystrobin on downy mildew pathogens of cucumber

| Name of agent | $EC_{50}$ (μg/ml) | ATI | TTI | Co-toxicity coefficient (CTC) |
|---|---|---|---|---|
| Polyhexamethylene biguanide hydrochloride:azoxystrobin = 1:1 | 2.07 | 203.38 | 86.170 | 236.02 |
| Polyhexamethylene biguanide hydrochloride:azoxystrobin = 1:10 | 2.54 | 165.75 | 74.855 | 221.43 |
| Polyhexamethylene biguanide hydrochloride:azoxystrobin = 1:30 | 4.18 | 100.72 | 73.232 | 137.54 |
| Polyhexamethylene biguanide hydrochloride:azoxystrobin = 1:50 | 4.62 | 91.13 | 72.882 | 125.04 |

The results (in Table 3) show that the control effect of the combination of polyhexamethylene biguanide hydrochloride with azoxystrobin on downy mildew of cucumber is significantly improved, suggesting that the combination has an obvious synergistic effect on downy mildew pathogens of cucumber. Especially when polyhexamethylene biguanide hydrochloride is mixed with azoxystrobin at a ratio ranging from 1:30 to 30:1, the co-toxicity coefficient of polyhexamethylene biguanide hydrochloride and azoxystrobin is always above 135, and the synergistic effect is obvious.

(4) Toxicity Test of Polyhexamethylene Biguanide Hydrochloride Combined with Fenamidone on Downy Mildew Pathogens of Cucumber

TABLE 4

Toxicity test result analysis of polyhexamethylene biguanide hydrochloride combined with fenamidone on downy mildew pathogens of cucumber

| Name of agent | $EC_{50}$ (μg/ml) | ATI | TTI | Co-toxicity coefficient (CTC) |
|---|---|---|---|---|
| Polyhexamethylene biguanide hydrochloride | 5.51 | 100 | / | / |
| Fenamidone | 5.12 | 107.62 | / | / |
| Polyhexamethylene biguanide hydrochloride:fenamidone = 50:1 | 4.49 | 122.72 | 100.149 | 122.537 |
| Polyhexamethylene biguanide hydrochloride:fenamidone = 30:1 | 4.13 | 133.56 | 100.246 | 133.232 |
| Polyhexamethylene biguanide hydrochloride:fenamidone = 10:1 | 3.69 | 149.35 | 100.693 | 148.322 |
| Polyhexamethylene biguanide hydrochloride:fenamidone = 1:1 | 2.69 | 205.09 | 103.81 | 197.563 |
| Polyhexamethylene biguanide hydrochloride:fenamidone = 1:10 | 2.72 | 202.57 | 106.927 | 189.447 |
| Polyhexamethylene biguanide hydrochloride:fenamidone = 1:30 | 3.9 | 141.28 | 107.374 | 131.577 |
| Polyhexamethylene biguanide hydrochloride:fenamidone = 1:50 | 4.23 | 130.26 | 107.471 | 121.205 |

The results (in Table 4) show that the control effect of the combination of polyhexamethylene biguanide hydrochloride with fenamidone on downy mildew of cucumber is significantly improved, suggesting that the combination has an obvious synergistic effect on downy mildew pathogens of cucumber. Especially when polyhexamethylene biguanide hydrochloride is mixed with fenamidone at a ratio ranging from 1:30 to 30:1, the co-toxicity coefficient of polyhexamethylene biguanide hydrochloride and fenamidone is always above 130, and the synergistic effect is obvious.

(5) Toxicity Test of Polyhexamethylene Biguanide Hydrochloride Combined with Dithianon on Downy Mildew Pathogens of Cucumber

TABLE 5

Toxicity test result analysis of polyhexamethylene biguanide hydrochloride combined with dithianon on downy mildew pathogens of cucumber

| Name of agent | $EC_{50}$ (μg/ml) | ATI | TTI | Co-toxicity coefficient (CTC) |
|---|---|---|---|---|
| Polyhexamethylene biguanide hydrochloride | 4.72 | 100 | / | / |
| Dithianon | 5.34 | 88.39 | / | / |
| Polyhexamethylene biguanide hydrochloride:dithianon = 50:1 | 4.06 | 116.26 | 99.772 | 116.526 |
| Polyhexamethylene biguanide hydrochloride:dithianon = 30:1 | 3.69 | 127.91 | 99.625 | 128.391 |
| Polyhexamethylene biguanide hydrochloride:dithianon = 10:1 | 2.83 | 166.78 | 98.945 | 168.558 |
| Polyhexamethylene biguanide hydrochloride:dithianon = 1:1 | 2.92 | 161.64 | 94.195 | 171.601 |
| Polyhexamethylene biguanide hydrochloride:dithianon = 1:10 | 2.83 | 166.78 | 89.445 | 186.461 |
| Polyhexamethylene biguanide hydrochloride:dithianon = 1:30 | 4.06 | 116.26 | 88.765 | 130.975 |
| Polyhexamethylene biguanide hydrochloride:dithianon = 1:50 | 4.38 | 107.76 | 88.618 | 121.601 |

The results (in Table 5) show that the control effect of the combination of polyhexamethylene biguanide hydrochloride with dithianon on downy mildew of cucumber is significantly improved, suggesting that the combination has an obvious synergistic effect on downy mildew pathogens of cucumber. Especially when polyhexamethylene biguanide or an agriculturally acceptable salt thereof is mixed with dithianon at a ratio ranging from 1:30 to 30:1, the co-toxicity coefficient of polyhexamethylene biguanide hydrochloride and dithianon is always above 125, and the synergistic effect is obvious.

(6) Toxicity Test of Polyhexamethylene Biguanide Hydrochloride Combined with Polyoxin on Downy Mildew Pathogens of Cucumber

TABLE 6

Toxicity test result analysis of polyhexamethylene biguanide hydrochloride combined with polyoxin on downy mildew pathogens of cucumber

| Name of agent | $EC_{50}$ (μg/ml) | ATI | TTI | Co-toxicity coefficient (CTC) |
|---|---|---|---|---|
| Polyhexamethylene biguanide hydrochloride | 4.71 | 100 | / | / |
| Polyoxin | 5.24 | 89.89 | / | / |
| Polyhexamethylene biguanide hydrochloride:polyoxin = 50:1 | 4.01 | 117.46 | 99.802 | 117.689 |
| Polyhexamethylene biguanide hydrochloride:polyoxin = 30:1 | 3.80 | 123.95 | 99.674 | 124.353 |
| Polyhexamethylene biguanide hydrochloride:polyoxin = 10:1 | 3.49 | 134.96 | 99.081 | 136.209 |
| Polyhexamethylene biguanide hydrochloride:polyoxin = 1:1 | 2.99 | 157.53 | 94.945 | 165.912 |
| Polyhexamethylene biguanide hydrochloride:polyoxin = 1:10 | 3.32 | 141.87 | 90.809 | 156.226 |
| Polyhexamethylene biguanide hydrochloride:polyoxin = 1:30 | 4.3 | 109.53 | 90.216 | 121.414 |
| Polyhexamethylene biguanide hydrochloride:polyoxin = 1:50 | 4.53 | 103.97 | 90.088 | 115.413 |

The results (in Table 6) show that the control effect of the combination of polyhexamethylene biguanide hydrochloride with polyoxin on downy mildew of cucumber is significantly improved, suggesting that the combination has an obvious synergistic effect on downy mildew pathogens of cucumber.

(7) Toxicity Test of Polyhexamethylene Biguanide Hydrochloride Combined with Zoxamide on Downy Mildew Pathogens of Cucumber significantly improved, suggesting that the combination has an obvious synergistic effect on downy mildew pathogens of cucumber. Especially when polyhexamethylene biguanide hydrochloride is mixed with zoxamide at a ratio ranging from 1:30 to 30:1, the co-toxicity coefficient of polyhexamethylene biguanide hydrochloride and zoxamide is always above 130, and the synergistic effect is obvious.

TABLE 7

Toxicity test result analysis of polyhexamethylene biguanide hydrochloride combined with zoxamide on downy mildew pathogens of cucumber

| Name of agent | $EC_{50}$ (μg/ml) | ATI | TTI | Co-toxicity coefficient (CTC) |
|---|---|---|---|---|
| Polyhexamethylene biguanide hydrochloride | 4.89 | 100 | / | / |
| Zoxamide | 5.11 | 95.69 | / | / |
| Polyhexamethylene biguanide hydrochloride:zoxamide = 50:1 | 4.19 | 116.71 | 99.915 | 116.806 |
| Polyhexamethylene biguanide hydrochloride:zoxamide = 30:1 | 4.05 | 120.74 | 99.861 | 120.909 |
| Polyhexamethylene biguanide hydrochloride:zoxamide = 10:1 | 3.39 | 144.25 | 99.608 | 144.815 |
| Polyhexamethylene biguanide hydrochloride:zoxamide = 1:1 | 3.19 | 153.29 | 97.845 | 156.668 |
| Polyhexamethylene biguanide hydrochloride:zoxamide = 1:10 | 3.42 | 142.98 | 96.082 | 148.813 |
| Polyhexamethylene biguanide hydrochloride:zoxamide = 1:30 | 4.02 | 121.64 | 95.829 | 126.936 |
| Polyhexamethylene biguanide hydrochloride:zoxamide = 1:50 | 4.16 | 117.55 | 95.775 | 122.734 |

The results (in Table 7) show that the control effect of the combination of polyhexamethylene biguanide hydrochloride with zoxamide on downy mildew of cucumber is (8) Toxicity Test of Polyhexamethylene Biguanide Hydrochloride Combined with Acibenzolar on Downy Mildew Pathogens of Cucumber

TABLE 8

Toxicity test result analysis of polyhexamethylene biguanide hydrochloride combined with acibenzolar on downy mildew pathogens of cucumber

| Name of agent | $EC_{50}$ (μg/ml) | ATI | TTI | Co-toxicity coefficient (CTC) |
|---|---|---|---|---|
| Polyhexamethylene biguanide hydrochloride | 4.92 | 100 | / | / |
| Acibenzolar | 5.38 | 91.45 | / | / |
| Polyhexamethylene biguanide hydrochloride:acibenzolar = 50:1 | 4.21 | 116.865 | 99.832 | 117.062 |
| Polyhexamethylene biguanide hydrochloride:acibenzolar = 30:1 | 4.03 | 122.084 | 99.724 | 122.422 |
| Polyhexamethylene biguanide hydrochloride:acibenzolar = 10:1 | 3.13 | 157.188 | 99.223 | 158.419 |
| Polyhexamethylene biguanide hydrochloride:acibenzolar = 1:1 | 3.19 | 154.232 | 95.725 | 161.120 |
| Polyhexamethylene biguanide hydrochloride:acibenzolar = 1:10 | 3.32 | 148.193 | 92.227 | 160.683 |
| Polyhexamethylene biguanide hydrochloride:acibenzolar = 1:30 | 3.87 | 127.132 | 91.726 | 138.600 |
| Polyhexamethylene biguanide hydrochloride:acibenzolar = 1:50 | 4.53 | 108.609 | 91.618 | 118.545 |

The results (in Table 8) show that the control effect of the combination of polyhexamethylene biguanide hydrochloride with acibenzolar on downy mildew of cucumber is significantly improved, suggesting that the combination has an obvious synergistic effect on downy mildew pathogens of cucumber. Especially when polyhexamethylene biguanide hydrochloride is mixed with acibenzolar at a ratio ranging from 1:30 to 30:1, the co-toxicity coefficient of polyhexamethylene biguanide hydrochloride and acibenzolar is always above 130, and the synergistic effect is obvious.

(9) Toxicity Test of Polyhexamethylene Biguanide Hydrochloride Combined with Fluazinam on Downy Mildew Pathogens of Cucumber an obvious synergistic effect on downy mildew pathogens of cucumber. Especially when polyhexamethylene biguanide hydrochloride is mixed with fluazinam at a ratio ranging from 1:30 to 30:1, the co-toxicity coefficient of polyhexamethylene biguanide hydrochloride and fluazinam is always above 120, and the synergistic effect is obvious.

2. Toxicity test of polyhexamethylene biguanide hydrochloride combined respectively with difenoconazole, epoxiconazole, prothioconazole, pyraclostrobin, trifloxystrobin, picoxystrobin, thifluzamide, iprodione, and cyprodinil on rust pathogens of wheat. The test method was the same as above.

TABLE 9

Toxicity test result analysis of polyhexamethylene biguanide hydrochloride combined with fluazinam on downy mildew pathogens of cucumber

| Name of agent | $EC_{50}$ (µg/ml) | ATI | TTI | Co-toxicity coefficient (CTC) |
|---|---|---|---|---|
| Polyhexamethylene biguanide hydrochloride | 5.08 | 100 | / | / |
| Fluazinam | 5.19 | 97.88 | / | / |
| Polyhexamethylene biguanide hydrochloride:fluazinam = 50:1 | 4.19 | 121.241 | 99.958 | 121.292 |
| Polyhexamethylene biguanide hydrochloride:fluazinam = 30:1 | 4.03 | 126.055 | 99.932 | 126.141 |
| Polyhexamethylene biguanide hydrochloride:fluazinam = 10:1 | 3.5 | 145.143 | 99.807 | 145.424 |
| Polyhexamethylene biguanide hydrochloride:fluazinam = 1:1 | 3.09 | 164.401 | 98.94 | 166.162 |
| Polyhexamethylene biguanide hydrochloride:fluazinam = 1:10 | 3.29 | 154.407 | 98.073 | 157.441 |
| Polyhexamethylene biguanide hydrochloride:fluazinam = 1:30 | 3.91 | 129.923 | 97.948 | 132.645 |
| Polyhexamethylene biguanide hydrochloride:fluazinam = 1:50 | 4.47 | 113.647 | 97.922 | 116.059 |

The results (in Table 9) show that the control effect of the combination of polyhexamethylene biguanide hydrochloride with fluazinam on downy mildew of cucumber is significantly improved, suggesting that the combination has (1) Toxicity Test of Polyhexamethylene Biguanide Hydrochloride Combined with Difenoconazole on Rust Pathogens of Wheat

TABLE 10

Toxicity test result analysis of polyhexamethylene biguanide hydrochloride combined with difenoconazole on rust pathogens of wheat

| Name of agent | $EC_{50}$ (µg/ml) | ATI | TTI | Co-toxicity coefficient (CTC) |
|---|---|---|---|---|
| Polyhexamethylene biguanide hydrochloride | 5.82 | 100 | / | / |
| Difenoconazole | 5.45 | 106.79 | / | / |
| Polyhexamethylene biguanide hydrochloride:difenoconazole = 50:1 | 4.92 | 118.293 | 100.133 | 118.136 |
| Polyhexamethylene biguanide hydrochloride:difenoconazole = 30:1 | 4.73 | 123.044 | 100.219 | 122.776 |
| Polyhexamethylene biguanide hydrochloride:difenoconazole = 10:1 | 3.52 | 165.341 | 100.617 | 164.327 |
| Polyhexamethylene biguanide hydrochloride:difenoconazole = 1:1 | 3.12 | 186.538 | 103.395 | 180.413 |
| Polyhexamethylene biguanide hydrochloride:difenoconazole = 1:10 | 3.41 | 170.674 | 106.173 | 160.751 |
| Polyhexamethylene biguanide hydrochloride:difenoconazole = 1:30 | 4.16 | 139.904 | 106.571 | 131.278 |
| Polyhexamethylene biguanide hydrochloride:difenoconazole = 1:50 | 4.90 | 118.776 | 106.657 | 111.362 |

The results (in Table 10) show that the control effect of the combination of polyhexamethylene biguanide hydrochloride with difenoconazole on rust of wheat is significantly improved, suggesting that the combination has an obvious synergistic effect on rust pathogens of wheat. Especially when polyhexamethylene biguanide hydrochloride is mixed with difenoconazole at a ratio ranging from 1:30 to 30:1, the co-toxicity coefficient of polyhexamethylene biguanide hydrochloride and difenoconazole is always above 120, and the synergistic effect is obvious.

(2) Toxicity Test of Polyhexamethylene Biguanide Hydrochloride Combined with Epoxiconazole on Rust Pathogens of Wheat

TABLE 11

Toxicity test result analysis of polyhexamethylene biguanide hydrochloride combined with epoxiconazole on rust pathogens of wheat

| Name of agent | $EC_{50}$ (μg/ml) | ATI | TTI | Co-toxicity coefficient (CTC) |
|---|---|---|---|---|
| Polyhexamethylene biguanide hydrochloride | 5.69 | 100 | / | / |
| Epoxiconazole | 5.29 | 107.56 | / | / |
| Polyhexamethylene biguanide hydrochloride:epoxiconazole = 50:1 | 4.85 | 117.32 | 100.148 | 117.146 |
| Polyhexamethylene biguanide hydrochloride:epoxiconazole = 30:1 | 4.65 | 122.37 | 100.244 | 122.068 |
| Polyhexamethylene biguanide hydrochloride:epoxiconazole = 10:1 | 3.42 | 166.37 | 100.687 | 165.239 |
| Polyhexamethylene biguanide hydrochloride:epoxiconazole = 1:1 | 3.04 | 187.17 | 103.78 | 180.354 |
| Polyhexamethylene biguanide hydrochloride:epoxiconazole = 1:10 | 3.39 | 167.85 | 106.873 | 157.052 |
| Polyhexamethylene biguanide hydrochloride:epoxiconazole = 1:30 | 4.11 | 138.44 | 107.316 | 129.005 |
| Polyhexamethylene biguanide hydrochloride:epoxiconazole = 1:50 | 4.76 | 119.54 | 107.412 | 111.289 |

The results (in Table 11) show that the control effect of the combination of polyhexamethylene biguanide hydrochloride with epoxiconazole on rust of wheat is significantly improved, suggesting that the combination has an obvious synergistic effect on rust pathogens of wheat. Especially when polyhexamethylene biguanide hydrochloride is mixed with epoxiconazole at a ratio ranging from 1:30 to 30:1, the co-toxicity coefficient of polyhexamethylene biguanide hydrochloride and epoxiconazole is always above 120, and the synergistic effect is obvious.

(3) Toxicity Test of Polyhexamethylene Biguanide Hydrochloride Combined with Prothioconazole on Rust Pathogens of Wheat

TABLE 12

Toxicity test result analysis of polyhexamethylene biguanide hydrochloride combined with prothioconazole on rust pathogens of wheat

| Name of agent | $EC_{50}$ (μg/ml) | ATI | TTI | Co-toxicity coefficient (CTC) |
|---|---|---|---|---|
| Polyhexamethylene biguanide hydrochloride | 5.59 | 100 | / | / |
| Prothioconazole | 5.12 | 109.18 | / | / |
| Polyhexamethylene biguanide hydrochloride:prothioconazole = 50:1 | 4.91 | 113.85 | 100.18 | 113.645 |
| Polyhexamethylene biguanide hydrochloride:prothioconazole = 30:1 | 4.33 | 129.10 | 100.296 | 128.718 |
| Polyhexamethylene biguanide hydrochloride:prothioconazole = 10:1 | 3.37 | 165.88 | 100.835 | 164.502 |
| Polyhexamethylene biguanide hydrochloride:prothioconazole = 1:1 | 3.11 | 179.74 | 104.59 | 171.855 |
| Polyhexamethylene biguanide hydrochloride:prothioconazole = 1:10 | 3.41 | 163.93 | 108.345 | 151.303 |
| Polyhexamethylene biguanide hydrochloride:prothioconazole = 1:30 | 4.04 | 138.37 | 108.884 | 127.077 |
| Polyhexamethylene biguanide hydrochloride:prothioconazole = 1:50 | 4.69 | 119.19 | 109.000 | 109.348 |

The results (in Table 12) show that the control effect of the combination of polyhexamethylene biguanide hydrochloride with prothioconazole on rust of wheat is significantly improved, suggesting that the combination has an obvious synergistic effect on rust pathogens of wheat. Especially when polyhexamethylene biguanide hydrochloride is mixed with prothioconazole at a ratio ranging from 1:30 to 30:1, the co-toxicity coefficient of polyhexamethylene biguanide hydrochloride and prothioconazole is always above 120, and the synergistic effect is obvious.

(4) Toxicity Test of Polyhexamethylene Biguanide Hydrochloride Combined with Pyraclostrobin on Rust Pathogens of Wheat

TABLE 13

Toxicity test result analysis of polyhexamethylene biguanide hydrochloride combined with pyraclostrobin on rust pathogens of wheat

| Name of agent | $EC_{50}$ (µg/ml) | ATI | TTI | Co-toxicity coefficient (CTC) |
|---|---|---|---|---|
| Polyhexamethylene biguanide hydrochloride | 5.45 | 100 | / | / |
| Pyraclostrobin | 4.98 | 109.44 | / | / |
| Polyhexamethylene biguanide hydrochloride:pyraclostrobin = 50:1 | 4.83 | 112.84 | 100.185 | 112.628 |
| Polyhexamethylene biguanide hydrochloride:pyraclostrobin = 30:1 | 4.24 | 128.54 | 100.305 | 128.147 |
| Polyhexamethylene biguanide hydrochloride:pyraclostrobin = 10:1 | 3.46 | 157.51 | 100.858 | 156.174 |
| Polyhexamethylene biguanide hydrochloride:pyraclostrobin = 1:1 | 3.03 | 179.87 | 104.72 | 171.761 |
| Polyhexamethylene biguanide hydrochloride:pyraclostrobin = 1:10 | 3.51 | 155.27 | 108.582 | 142.999 |
| Polyhexamethylene biguanide hydrochloride:pyraclostrobin = 1:30 | 4.11 | 132.60 | 109.135 | 121.504 |
| Polyhexamethylene biguanide hydrochloride:pyraclostrobin = 1:50 | 4.57 | 119.26 | 109.255 | 109.154 |

The results (in Table 13) show that the control effect of the combination of polyhexamethylene biguanide hydrochloride with pyraclostrobin on rust of wheat is significantly improved, suggesting that the combination has an obvious synergistic effect on rust pathogens of wheat. Especially when polyhexamethylene biguanide hydrochloride is mixed with pyraclostrobin at a ratio ranging from 1:30 to 30:1, the co-toxicity coefficient of polyhexamethylene biguanide hydrochloride and pyraclostrobin is always above 120, and the synergistic effect is obvious.

(5) Toxicity Test of Polyhexamethylene Biguanide Hydrochloride Combined with Trifloxystrobin on Rust Pathogens of Wheat

TABLE 14

Toxicity test result analysis of polyhexamethylene biguanide hydrochloride combined with trifloxystrobin on rust pathogens of wheat

| Name of agent | $EC_{50}$ (μg/ml) | ATI | TTI | Co-toxicity coefficient (CTC) |
|---|---|---|---|---|
| Polyhexamethylene biguanide hydrochloride | 5.12 | 100 | / | / |
| Trifloxystrobin | 4.75 | 107.79 | / | / |
| Polyhexamethylene biguanide hydrochloride:trifloxystrobin = 50:1 | 4.65 | 110.11 | 100.153 | 109.939 |
| Polyhexamethylene biguanide hydrochloride:trifloxystrobin = 30:1 | 4.12 | 124.27 | 100.251 | 123.961 |
| Polyhexamethylene biguanide hydrochloride:trifloxystrobin = 10:1 | 3.29 | 155.62 | 100.708 | 154.529 |
| Polyhexamethylene biguanide hydrochloride:trifloxystrobin = 1:1 | 3.03 | 168.98 | 103.895 | 162.642 |
| Polyhexamethylene biguanide hydrochloride:trifloxystrobin = 1:10 | 3.25 | 157.54 | 107.082 | 147.119 |
| Polyhexamethylene biguanide hydrochloride:trifloxystrobin = 1:30 | 3.91 | 130.95 | 107.539 | 121.766 |
| Polyhexamethylene biguanide hydrochloride:trifloxystrobin = 1:50 | 4.07 | 125.80 | 107.637 | 116.873 |

The results (in Table 14) show that the control effect of the combination of polyhexamethylene biguanide hydrochloride with trifloxystrobin on rust of wheat is significantly improved, suggesting that the combination has an obvious synergistic effect on rust pathogens of wheat. Especially when polyhexamethylene biguanide hydrochloride is mixed with trifloxystrobin at a ratio ranging from 1:30 to 30:1, the co-toxicity coefficient of polyhexamethylene biguanide hydrochloride and trifloxystrobin is always above 120, and the synergistic effect is obvious.

(6) Toxicity Test of Polyhexamethylene Biguanide Hydrochloride Combined with Picoxystrobin on Rust Pathogens of Wheat

TABLE 15

Toxicity test result analysis of polyhexamethylene biguanide hydrochloride combined with picoxystrobin on rust pathogens of wheat

| Name of agent | $EC_{50}$ (μg/ml) | ATI | TTI | Co-toxicity coefficient (CTC) |
|---|---|---|---|---|
| Polyhexamethylene biguanide hydrochloride | 4.98 | 100 | / | / |
| Picoxystrobin | 5.68 | 87.68 | / | / |
| Polyhexamethylene biguanide hydrochloride:picoxystrobin = 50:1 | 4.43 | 112.42 | 99.758 | 112.693 |
| Polyhexamethylene biguanide hydrochloride:picoxystrobin = 30:1 | 4.02 | 123.88 | 99.603 | 124.374 |
| Polyhexamethylene biguanide hydrochloride:picoxystrobin = 10:1 | 3.1 | 160.65 | 98.88 | 162.470 |
| Polyhexamethylene biguanide hydrochloride:picoxystrobin = 1:1 | 3.04 | 163.82 | 93.84 | 174.574 |
| Polyhexamethylene biguanide hydrochloride:picoxystrobin = 1:10 | 3.19 | 156.11 | 88.80 | 175.800 |
| Polyhexamethylene biguanide hydrochloride:picoxystrobin = 1:30 | 4.54 | 109.69 | 88.077 | 124.539 |
| Polyhexamethylene biguanide hydrochloride:picoxystrobin = 1:50 | 4.7 | 105.96 | 87.922 | 120.516 |

The results (in Table 15) show that the control effect of the combination of polyhexamethylene biguanide hydrochloride with picoxystrobin on rust of wheat is significantly improved, suggesting that the combination has an obvious synergistic effect on rust pathogens of wheat. Especially when polyhexamethylene biguanide hydrochloride is mixed with picoxystrobin at a ratio ranging from 1:30 to 30:1, the co-toxicity coefficient of polyhexamethylene biguanide hydrochloride and picoxystrobin is always above 120, and the synergistic effect is obvious.

(7) Toxicity Test of Polyhexamethylene Biguanide Hydrochloride Combined with Thifluzamide on Rust Pathogens of Wheat

TABLE 16

Toxicity test result analysis of polyhexamethylene biguanide hydrochloride combined with thifluzamide on rust pathogens of wheat

| Name of agent | $EC_{50}$ (μg/ml) | ATI | TTI | Co-toxicity coefficient (CTC) |
|---|---|---|---|---|
| Polyhexamethylene biguanide hydrochloride | 5.56 | 100 | / | / |
| Thifluzamide | 5.12 | 108.59 | / | / |
| Polyhexamethylene biguanide hydrochloride:thifluzamide = 50:1 | 4.78 | 116.32 | 100.168 | 116.125 |
| Polyhexamethylene biguanide hydrochloride:thifluzamide = 30:1 | 4.28 | 129.91 | 100.277 | 129.551 |
| Polyhexamethylene biguanide hydrochloride:thifluzamide = 10:1 | 3.22 | 172.67 | 100.781 | 171.332 |
| Polyhexamethylene biguanide hydrochloride:thifluzamide = 1:1 | 3.3 | 168.48 | 104.295 | 161.542 |
| Polyhexamethylene biguanide hydrochloride:thifluzamide = 1:10 | 3.08 | 180.52 | 107.809 | 167.444 |
| Polyhexamethylene biguanide hydrochloride:thifluzamide = 1:30 | 4.18 | 133.01 | 108.313 | 122.802 |
| Polyhexamethylene biguanide hydrochloride:thifluzamide = 1:50 | 4.36 | 127.52 | 108.422 | 117.615 |

The results (in Table 16) show that the control effect of the combination of polyhexamethylene biguanide hydrochloride with thifluzamide on rust of wheat is significantly improved, suggesting that the combination has an obvious synergistic effect on rust pathogens of wheat. Especially when polyhexamethylene biguanide hydrochloride is mixed with thifluzamide at a ratio ranging from 1:30 to 30:1, the co-toxicity coefficient of polyhexamethylene biguanide hydrochloride and thifluzamide is always above 120, and the synergistic effect is obvious.

(8) Toxicity Test of Polyhexamethylene Biguanide Hydrochloride Combined with Iprodione on Rust Pathogens of Wheat

TABLE 17

Toxicity test result analysis of polyhexamethylene biguanide hydrochloride combined with iprodione on rust pathogens of wheat

| Name of agent | $EC_{50}$ (µg/ml) | ATI | TTI | Co-toxicity coefficient (CTC) |
|---|---|---|---|---|
| Polyhexamethylene biguanide hydrochloride | 5.89 | 100.00 | / | / |
| Iprodione | 5.35 | 110.09 | / | / |
| Polyhexamethylene biguanide hydrochloride:iprodione = 50:1 | 4.98 | 118.27 | 100.198 | 118.036 |
| Polyhexamethylene biguanide hydrochloride:iprodione = 30:1 | 4.46 | 132.06 | 100.325 | 131.632 |
| Polyhexamethylene biguanide hydrochloride:iprodione = 10:1 | 3.83 | 153.79 | 100.917 | 152.393 |
| Polyhexamethylene biguanide hydrochloride:iprodione = 1:1 | 3.32 | 177.41 | 105.045 | 168.890 |
| Polyhexamethylene biguanide hydrochloride:iprodione = 1:10 | 3.11 | 189.39 | 109.173 | 173.477 |
| Polyhexamethylene biguanide hydrochloride:iprodione = 1:30 | 4.20 | 140.24 | 109.765 | 127.764 |
| Polyhexamethylene biguanide hydrochloride:iprodione = 1:50 | 4.88 | 120.70 | 109.892 | 109.835 |

The results (in Table 17) show that the control effect of the combination of polyhexamethylene biguanide hydrochloride with iprodione on rust of wheat is significantly improved, suggesting that the combination has an obvious synergistic effect on rust pathogens of wheat. Especially when polyhexamethylene biguanide hydrochloride is mixed with iprodione at a ratio ranging from 1:30 to 30:1, the co-toxicity coefficient of polyhexamethylene biguanide hydrochloride and iprodione is always above 120, and the synergistic effect is obvious.

(9) Toxicity Test of Polyhexamethylene Biguanide Hydrochloride Combined with Cyprodinil on Rust Pathogens of Wheat

TABLE 18

Toxicity test result analysis of polyhexamethylene biguanide hydrochloride combined with cyprodinil on rust pathogens of wheat

| Name of agent | $EC_{50}$ (µg/ml) | ATI | TTI | Co-toxicity coefficient (CTC) |
|---|---|---|---|---|
| Polyhexamethylene biguanide hydrochloride | 5.25 | 100 | / | / |
| Cyprodinil | 5.87 | 89.44 | / | / |
| Polyhexamethylene biguanide hydrochloride:cyprodinil = | 4.83 | 108.70 | 99.793 | 108.925 |

TABLE 18-continued

Toxicity test result analysis of polyhexamethylene biguanide hydrochloride combined with cyprodinil on rust pathogens of wheat

| Name of agent | $EC_{50}$ (µg/ml) | ATI | TTI | Co-toxicity coefficient (CTC) |
|---|---|---|---|---|
| 50:1 | | | | |
| Polyhexamethylene biguanide hydrochloride:cyprodinil = | 4.36 | 120.41 | 99.659 | 120.822 |

TABLE 18-continued

Toxicity test result analysis of polyhexamethylene biguanide hydrochloride combined with cyprodinil on rust pathogens of wheat

| Name of agent | $EC_{50}$ (μg/ml) | ATI | TTI | Co-toxicity coefficient (CTC) |
|---|---|---|---|---|
| 30:1 |  |  |  |  |
| Polyhexamethylene biguanide hydrochloride:cyprodinil = 10:1 | 3.53 | 148.73 | 99.04 | 150.172 |
| Polyhexamethylene biguanide hydrochloride:cyprodinil = 1:1 | 3.22 | 163.04 | 94.72 | 172.128 |
| Polyhexamethylene biguanide hydrochloride:cyprodinil = 1:10 | 3.51 | 149.57 | 90.4 | 165.454 |
| Polyhexamethylene biguanide hydrochloride:cyprodinil = 1:30 | 4.65 | 112.90 | 89.781 | 125.750 |
| Polyhexamethylene biguanide hydrochloride:cyprodinil = 1:50 | 4.99 | 105.21 | 89.647 | 117.360 |

The results (in Table 18) show that the control effect of the combination of polyhexamethylene biguanide hydrochloride with cyprodinil on rust of wheat is significantly improved, suggesting that the combination has an obvious synergistic effect on rust pathogens of wheat. Especially when polyhexamethylene biguanide hydrochloride is mixed with cyprodinil at a ratio ranging from 1:30 to 30:1, the co-toxicity coefficient of polyhexamethylene biguanide hydrochloride and cyprodinil is always above 120, and the synergistic effect is obvious.

(II) Field Efficacy Test

Test method: in early stage of disease development, the first spray was given immediately, and then the second application was given after 7 days. Each treatment included 4 plots of 20 square meters each. The disease development before application and 10 days after the second application was statistically investigated. Samples were collected from 5 locations in each plot at random, and 5 plants were investigated at each location by investigating the percentages of the disease spot area on the leaves relative to the leaf area of the whole plant and grading. The disease index and the control effect were calculated.

$$\text{Disease index} = \frac{\sum \left( \begin{array}{c} \text{Number of leaves at each grade of disease development} \times \\ \text{Representative value of corresponding grade} \end{array} \right)}{\begin{array}{c} \text{Total number of leaves investigated} \times \\ \text{Representative value of highest level} \end{array}} \times 100$$

$$\text{Control effect (\%)} = \left( 1 - \frac{\begin{array}{c} \text{Disease index of control group before application} \times \\ \text{Disease index of treatment group after application} \end{array}}{\begin{array}{c} \text{Disease index of control group after application} \times \\ \text{Disease index of treatment group before application} \end{array}} \right) \times 100$$

Anticipated control effect (%) = $X+Y-XY/100$ (where $X$ and $Y$ are the control effect of a single agent)

Grade scale:
Grade 0: no disease spot;
Grade 1: number of disease spots on the leaf<5, and length<1 cm;
Grade 3: 6≤number of disease spots on the leaf≤10, and length of some disease spots>1 cm;
Grade 5: 11≤number of disease spots on the leaf≤25, some disease spots are contiguous, and the disease spot area is 10-25% of the leaf area;
Grade 7: number of disease spots on the leaf≥26, the disease spots are contiguous, and the disease spot area is 26-50% of the leaf area;
Grade 9: the disease spots are contiguous, and the disease spot area is above 50% of the leaf area, or all the leaves all wilted.

1. Field Efficacy Test of Polyhexamethylene Biguanide or a Salt Thereof Combined Respectively with Cyprodinil (or a Salt Thereof), Trifloxystrobin, Picoxystrobin, Fluazinam, and Thifluzamide for Controlling Rice Blast

TABLE 19

Field efficacy test of polyhexamethylene biguanide or a salt thereof combined with the above fungicides for rice blast

| No. | Treatment agent | Application rate (a.i.g/ha) | Disease index before application | Day 11 after the second application | |
|---|---|---|---|---|---|
| | | | | Disease index | Control effect (%) |
| Example 1 | 20% polyhexamethylene biguanide aqueous solution | 116 | 2.79 | 4.02 | 84.5 |
| | 50% cyprodinil wettable powder | 4 | 3.21 | 28.65 | 4.1 |
| | Anticipated control effect after mixing them | — | — | — | 85.1 |
| | 62% polyhexamethylene biguanide hydrochloride•cyprodinil wettable powder (polyhexamethylene biguanide hydrochloride:cyprodinil = 60:2) | 120 | 3.02 | 3.60 | 87.2 |
| Example 2 | 20% polyhexamethylene biguanide aqueous solution | 60 | 2.81 | 11.19 | 57.2 |
| | 50% cyprodinil wettable powder | 60 | 2.9 | 18.59 | 31.1 |
| | Anticipated control effect after mixing them | — | — | — | 70.5 |
| | 50% polyhexamethylene biguanide acetate•cyprodinil wettable powder (polyhexamethylene biguanide acetate:cyprodinil = 25:25) | 120 | 2.88 | 2.89 | 89.2 |

TABLE 19-continued

Field efficacy test of polyhexamethylene biguanide or a salt thereof combined with the above fungicides for rice blast

| No. | Treatment agent | Application rate (a.i.g/ha) | Disease index before application | Day 11 after the second application Disease index | Day 11 after the second application Control effect (%) |
|---|---|---|---|---|---|
| Example 3 | 20% polyhexamethylene biguanide aqueous solution | 3.7 | 2.69 | 22.98 | 8.2 |
|  | 50% cyprodinil wettable powder | 116.3 | 2.79 | 5.58 | 78.5 |
|  | Anticipated control effect after mixing them | — | — | — | 80.3 |
|  | 65% polyhexamethylene biguanide hydrochloride•cyprodinil wettable powder (polyhexamethylene biguanide hydrochloride:cyprodinil = 2:63) | 120 | 2.72 | 3.09 | 87.8 |
| Example 40 | 20% polyhexamethylene biguanide aqueous solution | 117 | 2.85 | 4.06 | 84.7 |
|  | 25% trifloxystrobin wettable powder | 3 | 2.98 | 26.48 | 4.5 |
|  | Anticipated control effect after mixing them | — | — | — | 85.4 |
|  | 88% polyhexamethylene biguanide•trifloxystrobin wettable powder (polyhexamethylene biguanide hydrochloride:Trifloxystrobin = 86:2) | 120 | 2.83 | 3.21 | 87.8 |
| Example 41 | 20% polyhexamethylene biguanide aqueous solution | 60 | 2.76 | 11.07 | 56.9 |
|  | 25% trifloxystrobin wettable powder | 60 | 3.04 | 15.93 | 43.7 |
|  | Anticipated control effect after mixing them | — | — | — | 75.7 |
|  | 50% polyhexamethylene biguanide carbonate•trifloxystrobin wettable powder (polyhexamethylene biguanide carbonate:trifloxystrobin = 25:25) | 120 | 2.93 | 3.57 | 86.9 |
| Example 42 | 20% polyhexamethylene biguanide aqueous solution | 2.8 | 3 | 26.02 | 6.8 |
|  | 25% trifloxystrobin wettable powder | 117.2 | 2.87 | 5.47 | 79.5 |
|  | Anticipated control effect after mixing them | — | — | — | 80.9 |
|  | 86% polyhexamethylene biguanide hydrochloride•trifloxystrobin wettable powder (polyhexamethylene biguanide hydrochloride:triflioxystrobin = 2:84) | 120 | 2.91 | 3.44 | 87.3 |
| Example 43 | 20% polyhexamethylene biguanide aqueous solution | 116 | 2.79 | 4.13 | 84.1 |
|  | 25% picoxystrobin wettable powder | 4 | 2.85 | 25.49 | 3.9 |
|  | Anticipated control effect after mixing them | — | — | — | 84.7 |
|  | 62% polyhexamethylene biguanide hydrochloride•picoxystrobin wettable powder (polyhexamethylene biguanide hydrochloride:picoxystrobin = 60:2) | 120 | 3.02 | 3.23 | 88.5 |
| Example 44 | 20% polyhexamethylene biguanide aqueous solution | 60 | 2.68 | 10.45 | 58.1 |
|  | 25% picoxystrobin wettable powder | 60 | 2.89 | 14.01 | 47.9 |
|  | Anticipated control effect after mixing them | — | — | — | 78.2 |
|  | 40% polyhexamethylene biguanide stearate•picoxystrobin wettable powder (polyhexamethylene biguanide stearate:picoxystrobin20:20) | 120 | 2.75 | 3.10 | 87.9 |
| Example 45 | 20% polyhexamethylene biguanide aqueous solution | 3.2 | 2.87 | 24.86 | 6.9 |
|  | 25% picoxystrobin wettable powder | 116.8 | 2.93 | 5.04 | 81.5 |
|  | Anticipated control effect after mixing them | — | — | — | 82.8 |
|  | 75% polyhexamethylene biguanide•picoxystrobin wettable powder (polyhexamethylene biguanide:picoxystrobin = 2:73) | 120 | 2.85 | 3.50 | 86.8 |
| Example 46 | 20% polyhexamethylene biguanide aqueous solution | 117 | 2.68 | 3.92 | 84.3 |
|  | 15% fluazinam wettable powder | 3 | 2.89 | 25.68 | 4.5 |
|  | Anticipated control effect after mixing them | — | — | — | 85.0 |
|  | 85% polyhexamethylene biguanide hydrochloride•fluazinam wettable powder (polyhexamethylene biguanide hydrochloride:fluazinam = 83:2) | 120 | 2.75 | 3.10 | 87.9 |

TABLE 19-continued

Field efficacy test of polyhexamethylene biguanide or a salt thereof combined with the above fungicides for rice blast

| No. | Treatment agent | Application rate (a.i.g/ha) | Disease index before application | Day 11 after the second application Disease index | Control effect (%) |
|---|---|---|---|---|---|
| Example 47 | 20% polyhexamethylene biguanide aqueous solution | 60 | 2.76 | 10.89 | 57.6 |
| | 15% fluazinam wettable powder | 60 | 2.85 | 13.23 | 50.1 |
| | Anticipated control effect after mixing them | — | — | — | 78.8 |
| | 40% polyhexamethylene biguanide•Fluazinam wettable powder (polyhexamethylene biguanide:fluazinam = 20:20) | 120 | 3.11 | 2.95 | 89.8 |
| Example 48 | 20% polyhexamethylene biguanide aqueous solution | 3.7 | 2.9 | 24.93 | 7.6 |
| | 15% fluazinam wettable powder | 116.3 | 2.85 | 4.72 | 82.2 |
| | Anticipated control effect after mixing them | — | — | — | 83.6 |
| | 65% polyhexamethylene biguanide acetate•fluazinam wettable powder (polyhexamethylene biguanide acetate:fluazinam = 2:63) | 120 | 2.79 | 2.88 | 88.9 |
| Example 49 | 20% polyhexamethylene biguanide aqueous solution | 117 | 3.21 | 5.02 | 83.2 |
| | 20% thifluzamide wettable powder | 3 | 3.16 | 27.90 | 5.1 |
| | Anticipated control effect after mixing them | — | — | — | 84.1 |
| | 82% polyhexamethylene biguanide hydrochloride•thifluzamide wettable powder (polyhexamethylene biguanide hydrochloride:thifluzamide = 80:2) | 120 | 3.29 | 3.77 | 87.7 |
| Example 50 | 20% polyhexamethylene biguanide aqueous solution | 60 | 3.05 | 11.86 | 58.2 |
| | 20% thifluzamide wettable powder | 60 | 3.25 | 13.28 | 56.1 |
| | Anticipated control effect after mixing them | — | — | — | 81.6 |
| | 50% polyhexamethylene biguanide•thifluzamide wettable powder (polyhexamethylene biguanide:thifluzamide = 25:25) | 120 | 2.99 | 3.48 | 87.5 |
| Example 51 | 20% polyhexamethylene biguanide aqueous solution | 3 | 3.3 | 28.62 | 6.8 |
| | 20% thifluzamide wettable powder | 117 | 3.31 | 5.51 | 82.1 |
| | Anticipated control effect after mixing them | — | — | — | 83.3 |
| | 82% polyhexamethylene biguanide stearate•thifluzamide wettable powder (polyhexamethylene biguanide stearate:thifluzamide = 2:80) | 120 | 3.12 | 3.51 | 87.9 |
| Water control (CK) | — | — | 2.85 | 26.52 | — |

The test results (in Table 19) show that the control effect of the combination of polyhexamethylene biguanide or a salt thereof with cyprodinil (or a salt thereof), trifloxystrobin, picoxystrobin, fluazinam, and thifluzamide respectively on rice blast is significantly improved, suggesting that the combination has an obvious synergistic effect on rice blast.

(2) Efficacy Test of Polyhexamethylene Biguanide or a Salt Thereof Combined Respectively with Epoxiconazole, Prothioconazole, Difenoconazole, Polyoxin, and Iprodione for Rice Sheath Blight

TABLE 20

Efficacy test of polyhexamethylene biguanide or a salt thereof combined respectively with the above fungicides for rice sheath blight

| No. | Treatment agent | Application rate (a.i.g/ha) | Disease index before application | Day 11 after the second application | |
|---|---|---|---|---|---|
| | | | | Disease index | Control effect (%) |
| Example 4 | 20% polyhexamethylene biguanide aqueous solution | 117 | 2.99 | 3.76 | 83.1 |
| | 12.6% epoxiconazole suspension | 3 | 3.32 | 23.75 | 3.9 |
| | Anticipated control effect after mixing them | — | — | — | 83.8 |
| | 85% polyhexamethylene biguanide hydrochloride•epoxiconazole wettable powder (polyhexamethylene biguanide hydrochloride:epoxiconazole = 83:2) | 120 | 3.12 | 3.04 | 86.9 |
| Example 5 | 20% polyhexamethylene biguanide aqueous solution | 60 | 3.21 | 10.68 | 55.3 |
| | 12.6% epoxiconazole suspension | 60 | 3.32 | 14.11 | 42.9 |
| | Anticipated control effect after mixing them | — | — | — | 74.5 |
| | 30% polyhexamethylene biguanide acetate•epoxiconazole wettable powder (polyhexamethylene biguanide acetate:epoxiconazole = 15:15) | 120 | 3.34 | 2.91 | 88.3 |
| Example 6 | 20% polyhexamethylene biguanide aqueous solution | 3.2 | 2.92 | 20.19 | 7.1 |
| | 12.6% epoxiconazole suspension | 116.8 | 2.87 | 5.08 | 76.2 |
| | Anticipated control effect after mixing them | — | — | — | 77.9 |
| | 75% polyhexamethylene biguanide carbonate•epoxiconazole wettable powder (polyhexamethylene biguanide carbonate:epoxiconazole = 2:73) | 120 | 2.98 | 3.04 | 86.3 |
| Example 16 | 20% polyhexamethylene biguanide aqueous solution | 117 | 2.76 | 3.39 | 83.5 |
| | 20% prothioconazole wettable powder | 3 | 2.92 | 20.82 | 4.2 |
| | Anticipated control effect after mixing them | — | — | — | 84.2 |
| | 85% polyhexamethylene biguanide hydrochloride•prothioconazole wettable powder (polyhexamethylene biguanide hydrochloride:prothioconazole = 83:2) | 120 | 2.79 | 2.64 | 87.3 |
| Example 17 | 20% polyhexamethylene biguanide aqueous solution | 60 | 2.98 | 9.94 | 55.2 |
| | 20% prothioconazole wettable powder | 60 | 3.32 | 12.75 | 48.4 |
| | Anticipated control effect after mixing them | — | — | — | 76.9 |
| | 50% polyhexamethylene biguanide•prothioconazole wettable powder (polyhexamethylene biguanide:prothioconazole = 25:25) | 120 | 2.99 | 2.63 | 88.2 |
| Example 18 | 20% polyhexamethylene biguanide aqueous solution | 2.8 | 3.21 | 22.43 | 6.1 |
| | 20% prothioconazole wettable powder | 117.2 | 2.87 | 5.08 | 76.2 |
| | Anticipated control effect after mixing them | — | — | — | 77.7 |

TABLE 20-continued

Efficacy test of polyhexamethylene biguanide or a salt thereof combined respectively with the above fungicides for rice sheath blight

| No. | Treatment agent | Application rate (a.i.g/ha) | Disease index before application | Day 11 after the second application | |
|---|---|---|---|---|---|
| | | | | Disease index | Control effect (%) |
| | 85% polyhexamethylene biguanide stearate•prothioconazole wettable powder (polyhexamethylene biguanide stearate:prothioconazole = 2:83) | 120 | 3.12 | 3.07 | 86.8 |
| Example 19 | 20% polyhexamethylene biguanide aqueous solution | 117.3 | 3.42 | 3.89 | 84.7 |
| | 18% difenoconazole suspension | 2.8 | 3.42 | 24.64 | 3.2 |
| | Anticipated control effect after mixing them | — | — | — | 85.2 |
| | 88% polyhexamethylene biguanide•difenoconazole wettable powder (polyhexamethylene biguanide:difenoconazole = 86:2) | 120 | 3.32 | 3.19 | 87.1 |
| Example 20 | 20% polyhexamethylene biguanide aqueous solution | 60 | 3.62 | 11.80 | 56.2 |
| | 18% difenoconazole suspension | 60 | 3.23 | 12.07 | 49.8 |
| | Anticipated control effect after mixing them | — | — | — | 78.0 |
| | 50% polyhexamethylene biguanide carbonate•difenoconazole wettable powder (polyhexamethylene biguanide carbonate:difenoconazole = 25:25) | 120 | 3.25 | 3.31 | 86.3 |
| Example 21 | 20% polyhexamethylene biguanide aqueous solution | 2.8 | 2.97 | 20.67 | 6.5 |
| | 18% difenoconazole suspension | 117.2 | 2.99 | 3.65 | 83.6 |
| | Anticipated control effect after mixing them | — | — | — | 84.7 |
| | 86% polyhexamethylene biguanide hydrochloride•difenoconazole wettable powder (polyhexamethylene biguanide hydrochloride:difenoconazole = 2:84) | 120 | 3.15 | 2.98 | 87.3 |
| Example 25 | 20% polyhexamethylene biguanide aqueous solution | 117.2 | 3.28 | 4.03 | 83.5 |
| | 20% polyoxin wettable powder | 2.8 | 3.32 | 23.77 | 3.8 |
| | Anticipated control effect after mixing them | — | — | — | 84.1 |
| | 85% polyhexamethylene biguanide hydrochloride•polyoxin wettable powder (polyhexamethylene biguanide hydrochloride:polyoxin = 83:2) | 120 | 2.75 | 2.42 | 88.2 |
| Example 26 | 20% polyhexamethylene biguanide aqueous solution | 60 | 2.76 | 9.00 | 56.2 |
| | 20% polyoxin wettable powder | 60 | 2.85 | 9.99 | 52.9 |
| | Anticipated control effect after mixing them | — | — | — | 79.4 |
| | 30% polyhexamethylene biguanide acetate•polyoxin wettable powder (polyhexamethylene biguanide acetate:polyoxin = 15:15) | 120 | 3.31 | 2.59 | 89.5 |
| Example 27 | 20% polyhexamethylene biguanide aqueous solution | 3.2 | 2.87 | 19.76 | 7.5 |
| | 20% polyoxin wettable powder | 116.8 | 2.79 | 3.22 | 84.5 |
| | Anticipated control effect after mixing them | — | — | — | 85.7 |
| | 75% polyhexamethylene biguanide carbonate•polyoxin wettable powder (polyhexamethylene biguanide carbonate:polyoxin = 2:73) | 120 | 2.98 | 2.71 | 87.8 |
| Example 28 | 20% polyhexamethylene biguanide aqueous solution | 116.1 | 3.43 | 4.42 | 82.7 |
| | 50% iprodione suspension | 3.9 | 3.11 | 21.80 | 5.8 |
| | Anticipated control effect after mixing them | — | — | — | 83.7 |

TABLE 20-continued

Efficacy test of polyhexamethylene biguanide or a salt thereof combined respectively with the above fungicides for rice sheath blight

| No. | Treatment agent | Application rate (a.i.g/ha) | Disease index before application | Day 11 after the second application | |
|---|---|---|---|---|---|
| | | | | Disease index | Control effect (%) |
| | 62% polyhexamethylene biguanide hydrochloride•iprodione wettable powder (polyhexamethylene biguanide hydrochloride:iprodione = 60:2) | 120 | 3.65 | 3.75 | 86.2 |
| Example 29 | 20% polyhexamethylene biguanide aqueous solution | 60 | 3.23 | 10.55 | 56.1 |
| | 50% iprodione suspension | 60 | 2.95 | 10.06 | 54.2 |
| | Anticipated control effect after mixing them | — | — | — | 79.9 |
| | 40% polyhexamethylene biguanide stearate•iprodione wettable powder (polyhexamethylene biguanide stearate:iprodione = 20:20) | 120 | 2.98 | 2.42 | 89.1 |
| Example 30 | 20% polyhexamethylene biguanide aqueous solution | 3.2 | 3.12 | 21.85 | 5.9 |
| | 50% iprodione suspension | 116.8 | 3.32 | 4.55 | 81.6 |
| | Anticipated control effect after mixing them | — | — | — | 82.7 |
| | 75% polyhexamethylene biguanide•iprodione wettable powder (polyhexamethylene biguanide:iprodione = 2:73) | 120 | 3.34 | 3.33 | 86.6 |
| Water control (CK) | | — | 3.21 | 23.89 | — |

The test results (in Table 20) show that the control effect of the combination of polyhexamethylene biguanide or a salt thereof with epoxiconazole, prothioconazole, difenoconazole, polyoxin, and iprodione respectively on sheath blight of rice is significantly improved, suggesting that the combination has an obvious synergistic effect on rice sheath blight.

(3) Efficacy Test of Polyhexamethylene Biguanide or a Salt Thereof Combined Respectively with Benthiavalicarb-Isopropyl, Zoxamide, Azoxystrobin, Fenamidone, Acibenzolar, Dithianon, Pyraclostrobin, and Dimethomorph for Downy Mildew of Grape

TABLE 21

Efficacy test of polyhexamethylene biguanide or a salt thereof combined respectively with the above fungicides for downy mildew of grape

| No. | Treatment agent | Application rate (a.i.g/ha) | Disease index before application | Day 11 after the second application | |
|---|---|---|---|---|---|
| | | | | Disease index | Control effect (%) |
| Example 7 | 20% polyhexamethylene biguanide aqueous solution | 130.6 | 3.75 | 4.61 | 82.6 |
| | 25% benthiavalicarb-isopropyl wettable powder | 4.4 | 3.92 | 26.51 | 4.3 |
| | Anticipated control effect after mixing them | — | — | — | 83.3 |
| | 62% polyhexamethylene biguanide hydrochloride•benthiavalicarb-isopropyl wettable powder (polyhexamethylene biguanide hydrochloride:benthiavalicarb-isopropyl = 60:2) | 135 | 3.87 | 3.69 | 86.5 |
| Example 8 | 20% polyhexamethylene biguanide aqueous solution | 67.5 | 3.96 | 15.03 | 46.3 |
| | 25% benthiavalicarb-isopropyl wettable powder | 67.5 | 3.89 | 16.91 | 38.5 |
| | Anticipated control effect after mixing them | — | — | — | 67.0 |
| | 40% polyhexamethylene biguanide stearate•benthiavalicarb-isopropyl wettable powder (polyhexamethylene biguanide stearate:benthiavalicarb-isopropyl = 20:20) | 135 | 3.98 | 3.35 | 88.1 |

TABLE 21-continued

Efficacy test of polyhexamethylene biguanide or a salt thereof combined respectively with the above fungicides for downy mildew of grape

| No. | Treatment agent | Application rate (a.i.g/ha) | Disease index before application | Day 11 after the second application | |
|---|---|---|---|---|---|
| | | | | Disease index | Control effect (%) |
| Example 9 | 20% polyhexamethylene biguanide aqueous solution | 3.6 | 3.89 | 25.26 | 8.1 |
| | 25% benthiavalicarb-isopropyl wettable powder | 126.4 | 3.82 | 6.16 | 77.2 |
| | Anticipated control effect after mixing them | — | — | — | 79.0 |
| | 75% polyhexamethylene biguanide•benthiavalicarb-isopropyl wettable powder (polyhexamethylene biguanide:benthiavalicarb-isopropyl = 2:73) | 135 | 3.72 | 3.60 | 86.3 |
| Example 10 | 20% polyhexamethylene biguanide aqueous solution | 130.2 | 3.89 | 4.65 | 83.1 |
| | 30% zoxamide wettable powder | 4.8 | 3.98 | 26.83 | 4.6 |
| | Anticipated control effect after mixing them | — | — | — | 83.9 |
| | 85% polyhexamethylene biguanide hydrochloride•zoxamide wettable powder (polyhexamethylene biguanide hydrochloride:zoxamide = 82:3) | 135 | 3.87 | 3.77 | 86.2 |
| Example 11 | 20% polyhexamethylene biguanide aqueous solution | 67.5 | 3.76 | 14.06 | 47.1 |
| | 30% zoxamide wettable powder | 67.5 | 4.04 | 16.22 | 43.2 |
| | Anticipated control effect after mixing them | — | — | — | 70.0 |
| | 60% polyhexamethylene biguanide•zoxamide wettable powder (polyhexamethylene biguanide:zoxamide = 30:30) | 135 | 3.93 | 3.58 | 87.1 |
| Example 12 | 20% polyhexamethylene biguanide aqueous solution | 3.6 | 3.87 | 25.38 | 7.2 |
| | 30% zoxamide wettable powder | 131.4 | 3.87 | 5.96 | 78.2 |
| | Anticipated control effect after mixing them | — | — | — | 79.8 |
| | 75% polyhexamethylene biguanide sulfate•zoxamide wettable powder (polyhexamethylene biguanide sulfate:zoxamide = 2:73) | 135 | 3.94 | 3.87 | 86.1 |
| Example 13 | 20% polyhexamethylene biguanide aqueous solution | 131.9 | 3.79 | 4.85 | 81.9 |
| | 25% azoxystrobin water dispersible granules | 3.1 | 3.82 | 26.02 | 3.6 |
| | Anticipated control effect after mixing them | — | — | — | 82.6 |
| | 88% polyhexamethylene biguanide hydrochloride•azoxystrobin wettable powder (polyhexamethylene biguanide hydrochloride:Azoxystrobin = 86:2) | 135 | 3.59 | 3.10 | 87.8 |
| Example 14 | 20% polyhexamethylene biguanide aqueous solution | 67.5 | 3.68 | 13.99 | 46.2 |
| | 25% azoxystrobin water dispersible granules | 67.5 | 3.85 | 14.91 | 45.2 |
| | Anticipated control effect after mixing them | — | — | — | 70.5 |
| | 50% polyhexamethylene biguanide•azoxystrobin wettable powder (polyhexamethylene biguanide:Azoxystrobin = 25:25) | 135 | 3.78 | 3.79 | 85.8 |
| Example 15 | 20% polyhexamethylene biguanide aqueous solution | 4.4 | 3.87 | 25.22 | 7.8 |
| | 25% azoxystrobin water dispersible granules | 130.5 | 3.92 | 5.51 | 80.1 |
| | Anticipated control effect after mixing them | — | — | — | 81.7 |

TABLE 21-continued

Efficacy test of polyhexamethylene biguanide or a salt thereof combined respectively with the above fungicides for downy mildew of grape

| No. | Treatment agent | Application rate (a.i.g/ha) | Disease index before application | Day 11 after the second application | |
|---|---|---|---|---|---|
| | | | | Disease index | Control effect (%) |
| | 62% polyhexamethylene biguanide acetate•azoxystrobin wettable powder (polyhexamethylene biguanide acetate:azoxystrobin = 2:60) | 135 | 3.81 | 3.34 | 87.6 |
| Example 22 | 20% polyhexamethylene biguanide aqueous solution | 130.6 | 3.65 | 4.62 | 82.1 |
| | 30% fenamidone wettable powder | 4.4 | 3.89 | 26.20 | 4.7 |
| | Anticipated control effect after mixing them | — | — | — | 82.9 |
| | 62% polyhexamethylene biguanide hydrochloride•fenamidone wettable powder (polyhexamethylene biguanide hydrochloride:fenamidone = 60:2) | 135 | 3.79 | 3.72 | 86.1 |
| Example 23 | 20% polyhexamethylene biguanide aqueous solution | 67.5 | 3.78 | 14.00 | 47.6 |
| | 30% fenamidone wettable powder | 67.5 | 3.85 | 15.10 | 44.5 |
| | Anticipated control effect after mixing them | — | — | — | 70.9 |
| | 50% polyhexamethylene biguanide acetate•fenamidone wettable powder (polyhexamethylene biguanide acetate:fenamidone = 25:25) | 135 | 3.91 | 3.81 | 86.2 |
| Example 24 | 20% polyhexamethylene biguanide aqueous solution | 4.2 | 3.86 | 25.12 | 7.9 |
| | 30% fenamidone wettable powder | 130.8 | 3.82 | 5.37 | 80.1 |
| | Anticipated control effect after mixing them | — | — | — | 81.7 |
| | 65% polyhexamethylene biguanide hydrochloride•fenamidone wettable powder (polyhexamethylene biguanide hydrochloride:fenamidone = 2:63) | 135 | 3.79 | 3.96 | 85.2 |
| Example 31 | 20% polyhexamethylene biguanide aqueous solution | 131.8 | 3.91 | 5.44 | 80.3 |
| | 15% acibenzolar wettable powder | 3.2 | 3.21 | 21.57 | 4.9 |
| | Anticipated control effect after mixing them | — | — | — | 81.3 |
| | 85% polyhexamethylene biguanide hydrochloride•acibenzolar wettable powder (polyhexamethylene biguanide hydrochloride:acibenzolar = 83:2) | 135 | 3.79 | 3.80 | 85.8 |
| Example 32 | 20% polyhexamethylene biguanide aqueous solution | 67.5 | 3.98 | 14.60 | 48.1 |
| | 15% acibenzolar wettable powder | 67.5 | 4.05 | 15.31 | 46.5 |
| | Anticipated control effect after mixing them | — | — | — | 72.2 |
| | 60% polyhexamethylene biguanide•acibenzolar wettable powder (polyhexamethylene biguanide:acibenzolar = 30:30) | 135 | 3.99 | 3.33 | 88.2 |
| Example 33 | 20% polyhexamethylene biguanide aqueous solution | 3.5 | 3.73 | 24.49 | 7.1 |
| | 15% acibenzolar wettable powder | 131.5 | 3.32 | 4.62 | 80.3 |
| | Anticipated control effect after mixing them | — | — | — | 81.7 |
| | 78% polyhexamethylene biguanide sulfate•acibenzolar wettable powder (polyhexamethylene biguanide sulfate:acibenzolar = 2:76) | 135 | 3.54 | 3.38 | 86.5 |
| Example 34 | 20% polyhexamethylene biguanide aqueous solution | 131.9 | 4.11 | 5.43 | 81.3 |
| | 22.7% dithianon suspension | 3.1 | 3.87 | 26.47 | 3.2 |
| | Anticipated control effect after mixing them | — | — | — | 81.9 |

TABLE 21-continued

Efficacy test of polyhexamethylene biguanide or a salt thereof combined respectively with the above fungicides for downy mildew of grape

| No. | Treatment agent | Application rate (a.i.g/ha) | Disease index before application | Day 11 after the second application | |
|---|---|---|---|---|---|
| | | | | Disease index | Control effect (%) |
| | 88% polyhexamethylene biguanide hydrochloride•dithianon wettable powder (polyhexamethylene biguanide hydrochloride:dithianon = 86:2) | 135 | 3.99 | 4.03 | 85.7 |
| Example 35 | 20% polyhexamethylene biguanide aqueous solution | 67.5 | 3.65 | 13.70 | 46.9 |
| | 22.7% dithianon suspension | 67.5 | 3.82 | 15.63 | 42.1 |
| | Anticipated control effect after mixing them | — | — | — | 69.3 |
| | 50% polyhexamethylene biguanide•dithianon wettable powder(polyhexamethylene biguanide:dithianon = 25:25) | 135 | 3.72 | 4.02 | 84.7 |
| Example 36 | 20% polyhexamethylene biguanide aqueous solution | 4.2 | 3.57 | 23.41 | 7.2 |
| | 22.7% dithianon suspension | 130.8 | 3.95 | 6.00 | 78.5 |
| | Anticipated control effect after mixing them | — | — | — | 80.0 |
| | 65% polyhexamethylene biguanide acetate•dithianon wettable powder (polyhexamethylene biguanide acetate:dithianon = 2:63) | 135 | 4.13 | 4.26 | 85.4 |
| Example 37 | 20% polyhexamethylene biguanide aqueous solution | 131.8 | 3.69 | 5.14 | 80.3 |
| | 18% pyraclostrobin wettable powder | 3.2 | 3.75 | 25.47 | 3.9 |
| | Anticipated control effect after mixing them | — | — | — | 81.1 |
| | 85% polyhexamethylene biguanide hydrochloride•pyraclostrobin wettable powder (polyhexamethylene biguanide hydrochloride:pyraclostrobin = 83:2) | 135 | 4.02 | 4.20 | 85.2 |
| Example 38 | 20% polyhexamethylene biguanide aqueous solution | 67.5 | | 0.00 | 46.4 |
| | 18% pyraclostrobin wettable powder | 67.5 | 3.69 | 14.92 | 42.8 |
| | Anticipated control effect after mixing them | — | — | — | 69.3 |
| | 50% polyhexamethylene biguanide•pyraclostrobin wettable powder (polyhexamethylene biguanide:pyraclostrobin = 25:25) | 135 | 3.79 | 3.27 | 87.8 |
| Example 39 | 20% polyhexamethylene biguanide aqueous solution | 3.3 | 3.83 | 25.25 | 6.7 |
| | 18% pyraclostrobin wettable powder | 131.7 | 3.93 | 5.50 | 80.2 |
| | Anticipated control effect after mixing them | — | — | — | 81.5 |
| | 82% polyhexamethylene biguanide stearate•pyraclostrobin wettable powder (polyhexamethylene biguanide stearate:pyraclostrobin = 2:80) | 135 | 3.74 | 3.94 | 85.1 |
| Example 40 | 20% polyhexamethylene biguanide aqueous solution | 131.9 | 3.87 | 4.95 | 81.9 |
| | 30% trifloxystrobin suspension | 3.1 | 4.02 | 27.42 | 3.5 |
| | Anticipated control effect after mixing them | — | — | — | 82.5 |
| | 88% polyhexamethylene biguanide•tri-floxystrobin wettable powder (polyhexamethylene biguanide:trifloxystrobin = 86:2) | 135 | 3.95 | 3.88 | 86.1 |
| Example 41 | 20% polyhexamethylene biguanide aqueous solution | 67.5 | 3.68 | 13.99 | 46.2 |
| | 30% trifloxystrobin suspension | 67.5 | 4.06 | 16.24 | 43.4 |
| | Anticipated control effect after mixing them | — | — | — | 69.5 |

TABLE 21-continued

Efficacy test of polyhexamethylene biguanide or a salt thereof combined respectively with the above fungicides for downy mildew of grape

| No. | Treatment agent | Application rate (a.i.g/ha) | Disease index before application | Day 11 after the second application | |
|---|---|---|---|---|---|
| | | | | Disease index | Control effect (%) |
| | 50% polyhexamethylene biguanide carbonate•trifloxystrobin wettable powder (polyhexamethylene biguanide carbonate:trifloxystrobin = 25:25) | 135 | 3.82 | 3.19 | 88.2 |
| Example 42 | 20% polyhexamethylene biguanide aqueous solution | 3.1 | 3.65 | 24.30 | 5.8 |
| | 30% trifloxystrobin suspension | 131.9 | 3.72 | 5.65 | 78.5 |
| | Anticipated control effect after mixing them | — | — | — | 79.7 |
| | 86% polyhexamethylene biguanide hydrochloride•trifloxystrobin wettable powder(polyhexamethylene biguanide hydrochloride:trifloxystrobin = 2:84) | 135 | 3.95 | 4.05 | 85.5 |
| Water control (CK) | — | — | 3.87 | 27.35 | — |

The test results (in Table 21) show that the control effect of the combination of polyhexamethylene biguanide or a salt thereof with benthiavalicarb-isopropyl, zoxamide, azoxystrobin, fenamidone, acibenzolar, dithianon, pyraclostrobin, and dimethomorph respectively on downy mildew of grape is significantly improved, suggesting that the combination has an obvious synergistic effect on downy mildew of grape.

What is claimed is:

1. A fungicidal composition having a synergistic effect, comprising active ingredients A and B, wherein the active ingredient A is polyhexamethylene biguanide or an agriculturally acceptable salt thereof, the active ingredient B is one selected from cyprodinil, epoxiconazole, benthiavalicarb-isopropyl, zoxamide, azoxystrobin, prothioconazole, difenoconazole, fenamidone, polyoxin, iprodione, acibenzolar, dithianon, pyraclostrobin, trifloxystrobin, picoxystrobin, fluazinam, thifluzamide, and dimethomorph, and a weight ratio of the active ingredient A to the active ingredient B is from 1:10 to 10:1.

2. The fungicidal composition according to claim 1, wherein the agriculturally acceptable salt of polyhexamethylene biguanide is one of polyhexamethylene biguanide hydrochloride, polyhexamethylene biguanide nitrate, polyhexamethylene biguanide carbonate, polyhexamethylene biguanide phosphate, polyhexamethylene biguanide sulfate, polyhexamethylene biguanide stearate, and polyhexamethylene biguanide acetate.

3. The fungicidal composition according to claim 1, wherein the agriculturally acceptable salt of polyhexamethylene biguanide is polyhexamethylene biguanide hydrochloride.

4. The fungicidal composition according to claim 1, comprising 6-92% by weight of the active ingredients and further comprising 94-8% by weight of pesticide adjuvants.

5. The fungicidal composition according to claim 4, which is prepared into pesticidally acceptable formations with the active ingredients and the pesticide adjuvants.

6. The fungicidal composition according to claim 5, which is in the form of a powder or a wettable powder prepared with the active ingredients and the pesticide adjuvants.

7. The fungicidal composition according to claim 1 is implemented to control at least one disease on crops in the agricultural area.

8. The fungicidal composition according to claim 1 is implemented to control at least one of cucumber downy mildew or wheat rust.

* * * * *